United States Patent
Lo et al.

(10) Patent No.: US 10,566,076 B2
(45) Date of Patent: Feb. 18, 2020

(54) CUSTOMIZED INTEGRATED CIRCUIT FOR SERIAL COMPARISON OF NUCLEOTIDE SEQUENCES

(71) Applicant: Microsoft Technology Licensing, LLC, Redmond, WA (US)

(72) Inventors: Daniel Lo, Bellevue, WA (US); Eric Chung, Woodinville, WA (US); Kalin Ovtcharov, Kirkland, WA (US); Ravindra Pandya, Clyde Hill, WA (US); David Heckerman, Santa Monica, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 505 days.

(21) Appl. No.: 15/349,725

(22) Filed: Nov. 11, 2016

(65) Prior Publication Data

US 2018/0137237 A1    May 17, 2018

(51) Int. Cl.
| | |
|---|---|
| *G01N 33/48* | (2006.01) |
| *G01N 33/50* | (2006.01) |
| *G16B 30/00* | (2019.01) |
| *G06F 7/02* | (2006.01) |

(52) U.S. Cl.
CPC .............. *G16B 30/00* (2019.02); *G06F 7/02* (2013.01)

(58) Field of Classification Search
None
See application file for complete search history.

(56) References Cited

U.S. PATENT DOCUMENTS

| | | |
|---|---|---|
| 7,917,302 B2 | 3/2011 | Rognes |
| 9,014,989 B2 | 4/2015 | McMillen et al. |
| 9,235,680 B2 | 1/2016 | Rooyen et al. |
| 9,342,652 B2 | 5/2016 | Van Rooyen et al. |
| 2007/0067108 A1 | 3/2007 | Buhler et al. |

(Continued)

OTHER PUBLICATIONS

Rognes et al. Six-fold speed-up of Smith-Waterman sequence database searches using parallel processing on common microprocessors. Bioinformatics, vol. 16, pp. 699-706. (Year: 2000).*

(Continued)

*Primary Examiner* — Russell S Negin
(74) *Attorney, Agent, or Firm* — Watson Patents, PLC; Vladan M. Vasiljevic

(57) ABSTRACT

Comparisons between two nucleotide sequences can be performed by customized integrated circuitry that can implement a Smith Waterman analysis in series, as opposed to the parallel implementations known in the art. Series performance enables such customized integrated circuitry to take advantage of optimizations, including enveloping thresholds that demarcate between cells of a two-dimensional matrix for which nucleotide comparisons are to be performed, and cells of the two-dimensional matrix for which no such comparison need be performed, and, instead, a value of zero can simply be entered. Additionally, such customized integrated circuitry facilitates the combination of multiple control units, each directing the comparison of a unique pair of nucleotides, with a single calculation engine that can generate values for individual cells of the two-dimensional matrices by which such pairs of nucleotides are compared.

20 Claims, 6 Drawing Sheets

(56) References Cited

U.S. PATENT DOCUMENTS

2008/0086274 A1    4/2008    Chamberlain et al.
2012/0239706 A1    9/2012    Steinfadt
2014/0172824 A1    6/2014    Musuvathi et al.

OTHER PUBLICATIONS

El-Wafa, et al., "Hardware Acceleration of Smith-Waterman Algorithm for short read DNA Alignment Using FPGA", In Proceedings of IEEE 40th Annual Computer Software and Applications Conference, Jun. 14, 2016, pp. 604-605.

Dydel, et al., "Large Scale Protein Sequence Alignment Using FPGA Reprogrammable Logic Devices", In Proceedings of 14th International Conference on Field Programmable Logic and Application, Aug. 30, 2004, pp. 23-32.

Fernandez, et al., "Multithreaded FPGA Acceleration of DNA Sequence Mapping", In Proceedings of IEEE Conference on High Performance Extreme Computing, Sep. 10, 2012, 6 pages.

Strengholt, et al., "Acceleration of the Smith-Waterman algorithm for DNA sequence alignment using an FPGA platform", In Bachelor Thesis, Jun. 27, 2013, 60 pages.

Benkrid, et al., "High Performance Biological Pairwise Sequence Alignment: FPGA versus GPU versus Cell BE versus GPP", In International Journal of Reconfigurable Computing, vol. 2012, Jan. 2012, pp. 1-15.

Yu, et al., "A Smith-Waterman Systolic Cell", In Proceedings of the 13th International Conference on Field Programmable Logic and Applications, Sep. 1, 2003, 10 pages.

Mahram, Atabak, "FPGA Acceleration of Sequence Analysis Tools in Bioinformatics", In Doctoral Dissertation, Sep. 6, 2016, 180 pages.

Zhang, et al., "Implementation of the Smith-Waterman Algorithm on a Reconfigurable Supercomputing Platform", In White Paper of Altera, Sep. 2007, pp. 1-18.

Meng, et al., "Modern Computational Techniques for the HMMER Sequence Analysis", In Journal of ISRN Bioinformatics, vol. 2013, Sep. 3, 2013, pp. 1-13.

"Smith-Waterman Algorithm", Retrieved on: Sep. 9, 2016 Available at: https://en.wikipedia.org/wiki/Smith%E2%80%93Waterman_algorithm.

"Burrows-Wheeler Aligner", Retrieved on: Sep. 9, 2016 Available at: http://bio-bwa.sourceforge.net/.

Houtgast, et al., "An FPGA-based systolic array to accelerate the BWA-MEM genomic mapping algorithm", In Proceedings of International Conference on Embedded Computer Systems: Architectures, Modeling, and Simulation, Jul. 19, 2015, pp. 221-227.

Ahmed, et al., "Heterogeneous Hardware/Software Acceleration of the BWA-MEM DNA Alignment Algorithm", In Proceedings of the IEEE/ACM International Conference on Computer-Aided Design, Nov. 2, 2015, pp. 240-246.

\* cited by examiner

CUSTOMIZED INTEGRATED CIRCUIT FOR SERIAL COMPARISON OF NUCLEOTIDE SEQUENCES

BACKGROUND

Specialized processing devices can comprise processing circuitry that is pre-configured to perform a discrete set of computing operations more quickly than generalized central processing units. Application-Specific Integrated Circuits (ASICs) comprise integrated circuitry that is specifically designed to perform a specific set of operations or calculations, and, as such, can perform such operations or calculations more quickly, or more efficiently, than generalized central processing units. Field-Programmable Gate Arrays (FPGAs) likewise comprise integrated circuitry, typically in the form of programmable logic blocks comprised of individual microprocessor gates and other like integrated circuits, which can be programmed or designed to perform a specific set of operations or calculations more quickly, and more efficiently, then generalized central processing units.

One area in which customized integrated circuits, such as ASICs and FPGAs, are utilized to perform calculations is in the analysis of nucleotide sequences. As will be recognized by those skilled in the art, two strings of nucleotide sequences can be compared such that the manner in which they align can reveal important differences. One mechanism for performing such a local sequence alignment is the Smith Waterman algorithm. Prior efforts to perform Smith Waterman analysis utilizing customized integrated circuits have focused on performing the operations associated with sequence alignment in parallel. Indeed, the traditional mechanism by which most compute operations are implemented in customized integrated circuits, such as FPGAs, is to "unroll" any loop operations onto the spatial fabric of the FPGA so that they may be performed in parallel, and, thus, more quickly. However, within the context of Smith Waterman analysis, efforts to perform the operations associated with sequence alignment in parallel have required patches, or hacks, that themselves consume large portions of the spatial fabric of an FPGA. Moreover, parallel performance of Smith Waterman analysis operations instantiates a fixed amount of processing and, thereby, prevents optimization in specific instances.

SUMMARY

Comparisons between two nucleotide sequences can be performed by customized integrated circuitry that can implement a Smith Waterman analysis in series, as opposed to the parallel implementations known in the art. By performing Smith Waterman analysis in series, such customized integrated circuitry can be designed to take advantage of optimizations, including enveloping thresholds that can demarcate between cells of a two-dimensional matrix for which nucleotide comparisons are to be performed, and cells of the two-dimensional matrix for which no such comparison need be performed, and, instead, a value of zero can simply be entered. Additionally, such customized integrated circuitry can combine multiple control units, each directing the comparison of a unique pair of nucleotides, with a single calculation engine that can generate values for individual cells of the two-dimensional matrices by which such pairs of nucleotides are compared.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Additional features and advantages will be made apparent from the following detailed description that proceeds with reference to the accompanying drawings.

DESCRIPTION OF THE DRAWINGS

The following detailed description may be best understood when taken in conjunction with the accompanying drawings, of which.

DETAILED DESCRIPTION

Figure 1:
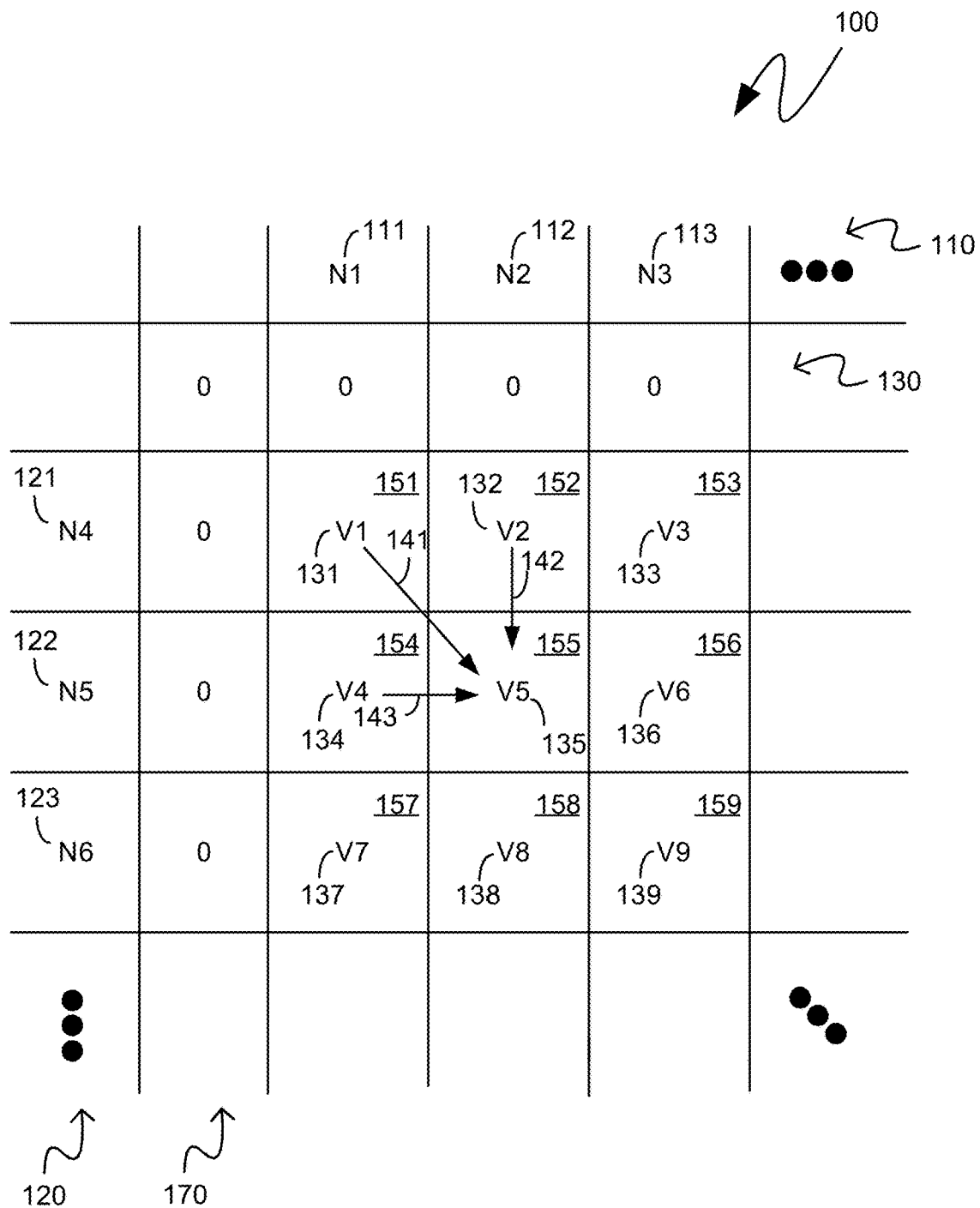
FIG. 1 is a block diagram of an exemplary two-dimensional matrix by which two nucleotides can be compared.

The following description relates to customized integrated circuitry that compares two strings of nucleotide sequences in a sequential manner, such as via a Smith Waterman analysis. Such customized integrated circuitry can comprise a calculation engine that can determine values, or "scores", for individual cells of a two-dimensional matrix through which to strings of nucleotide sequences can be compared. Additionally, such customized integrated circuitry can comprise one or more control units that can implement enveloping thresholds, which can demarcate between cells of the two-dimensional matrix for which nucleotide comparisons are to be performed, and cells of the two-dimensional matrix for which no such comparison need be performed, and, instead, a value of zero can simply be entered. Each control unit can control the comparison of a unique pair of nucleotide strings. However, multiple control units can utilize a single calculation engine, such as in an alternating manner, thereby decreasing a physical distance between control units and calculation engines, which, in turn, can provide for greater operational speed and processing frequency. Previously generated cell scores can be cached for subsequent use, with such a cache comprising a quantity of cell scores that is one greater than the quantity of cells in one row of the two-dimensional matrix.

The techniques described herein make reference to the Smith Waterman analysis mechanism by which a pair of nucleotide strings can be compared to detect, and quantify, similarities and differences between them. However, the mechanisms described are not limited to that specific mechanism, and can be utilized with any other analogous mechanism for comparing two sequences of items, selected from an appropriately limited set of items, whereby their comparison detects and quantifies the similarities and differences between them.

As utilized herein, the term "customized integrated circuit" means processing circuitry that is specifically optimized to perform a discrete subset of computer processing operations, or execute a discrete subset of computer-executable instructions, such that a computing result is achieved in a shorter duration of processing time than the processing time within which a general-purpose central processing unit, which was not so specifically optimized, would have achieved the same computing result. Consequently, as utilized herein, the adjective "specifically optimized" means that, prior to performance of the discrete subset of computer processing operations, or prior to execution of the discrete subset of computer-executable instructions, by the customized integrated circuit, the physical circuitry of the customized integrated circuit is either configured, manufactured, or modified to perform the discrete subset of computer processing operations or execute the discrete subset of computer-executable instructions to the exclusion of other computer processing operations or other computer-executable instructions. Such configuration or modification can occur either before, or after, the customized integrated circuit has already been manufactured. By contrast, as utilized herein, the term "general-purpose central processing unit" means a central processing unit whose physical circuitry that implements logic functionality, as opposed to the physical circuitry that provides for temporary storage of binary data, remains invariant and can execute any computer-executable instructions programmed for such a central processing unit. Additionally, as utilized herein, the terms "processing unit" and "processing circuitry" mean a collection of one or more hardware circuits that is capable of executing computer-executable instructions or performing computer processing operations.

For purposes of illustration, exemplary customized integrated circuits can include Application-Specific Integrated Circuits (ASICs), Field Programmable Gate Arrays (FPGAs) or other Very Large Scale Integrated circuits (VLSIs). By way of a hardware-specific example, the gate arrays of an FPGA can have particular voltages applied to specific gates in order to configure those gates to perform logic operations that result in the performance of one or more specific computer processing operations, such as those computer processing operations that implement the scoring described below. Consequently, as utilized herein, the terms "computer-readable media" and "computer storage media", as explicitly defined below, include the circuitry of a customized integrated circuit. Similarly, the term "computer-executable instructions", as utilized herein, includes the configuration of circuitry, such as by establishing or applying specific voltages to specific circuit elements, that enables such circuitry to perform computer processing operations in accordance with such computer-executable instructions.

Although not required, some of the descriptions below will be in the general context of computer-executable instructions, such as program modules, being executed by a computing device, including, specifically, a computing device comprising, or having access to, one or more customized integrated circuits directed to the serial performance of Smith Waterman analysis, such as detailed below. More specifically, the description will reference acts and symbolic representations of operations that are performed by one or more computing devices or peripherals, unless indicated otherwise. As such, it will be understood that such acts and operations, which are at times referred to as being computer-executed, include the manipulation by a processing unit of electrical signals representing data in a structured form. This manipulation transforms the data or maintains it at locations in memory, which reconfigures or otherwise alters the operation of the computing device or peripherals in a manner well understood by those skilled in the art. The data structures where data is maintained are physical locations that have particular properties defined by the format of the data.

Generally, program modules include routines, programs, objects, components, data structures, and the like that perform particular tasks or implement particular abstract data types. Moreover, those skilled in the art will appreciate that the computing devices need not be limited to conventional personal computers, and include other computing configurations, including hand-held devices, multi-processor systems, microprocessor based or programmable consumer electronics, network PCs, servers, minicomputers, mainframe computers, and the like. Similarly, the computing devices need not be limited to stand-alone computing devices, as the mechanisms may also be practiced in distributed computing environments where tasks are performed by remote processing devices that are linked through a communications network. In a distributed computing environment, program modules may be located in both local and remote memory storage devices.

With reference to FIG. 1, an exemplary two-dimensional matrix 100 is illustrated by which a comparison between two nucleotides can be accomplished, such as in accordance with Smith Waterman analysis. The exemplary matrix 100 is illustrated within the context of a comparison between two strings of nucleotides, or nucleotide sequences, namely the exemplary string of nucleotides 110 and the exemplary string of nucleotides 120. As visually indicated by the ellipses, the exemplary nucleotide sequence 110 can comprise the exemplary nucleotide 111, followed by, in the exemplary nucleotide sequence 110, the exemplary nucleotide 112, which can, in turn, be followed by the exemplary nucleotide 113, and so on. In a similar manner, the exemplary nucleotide sequence 120 can comprise the exemplary nucleotide 121, followed by, in the exemplary nucleotide sequence 120, exemplary nucleotide 122, which can, in turn, be followed by the exemplary nucleotide 123, and so on. The exemplary two-dimensional matrix 100, therefore, has one of its two dimensions delineated by nucleotides of a first nucleotide sequence, such as the exemplary string of nucleotides 110, and further has the other of its two dimensions delineated by nucleotides of a second nucleotide sequence, such as the exemplary string of nucleotides 120.

According to one aspect, nucleotides can be one of: Adenine, often represented by the letter "A", Guanine, often represented by the letter "G", Cytosine, often represented by the letter "C" and Thymine, often represented by the letter "T". For the purpose of forming a double helix, A typically matches with T and G typically matches with C. In comparing two sequences of nucleotides, the Smith Waterman calculation compares only one side of the helix and, consequently, within that context, "matches" means identical nucleotides. For example, with reference to the exemplary nucleotide sequences 110 and 120, a match could be the nucleotide A in nucleotide strand 110 and the same nucleotide A in strand 120 in a corresponding position within the nucleotide strand.

One purpose of the exemplary matrix 100 is to quantify how well the nucleotide sequence 110 matches the nucleotide sequence 120. Such a quantification, in accordance with Smith Waterman mechanisms, is often referred to as a total Smith Waterman "score", and is reflective of the quantity of "matches", "insertions," and "deletions" when comparing nucleotide strings 110 and 120. Within the exemplary matrix 100, each cell, such as the cells 151, 152, 153, 154, 155, 156, 157, 159 and 159, can have generated for it a score that is representative of how well the two nucleotides, from the exemplary nucleotide sequences 110 and 120, corresponding to that cell, match one another. Row 130 and column 170, in the exemplary two-dimensional matrix 100, illustrate the base of "0" on which each row and column start when utilizing Smith Waterman mechanisms to compare two nucleotide sequences. The score of a cell can further be representative of how well prior nucleotides, in the nucleotide sequences 110 and 120, matched one another. The exemplary matrix 100 illustrates exemplary values for each of the cells 151, 152, 153, 154, 155, 156, 157, 159 and 159, namely the values 131, 132, 133, 134, 135, 136, 137, 138, and 139, respectively.

According to one aspect, the scores of an individual cell can be generated based on a maximum, from among different values, each being generated in accordance with a particular comparison or prior score. For example, with reference to the exemplary cell 151, the score 131, assigned to the exemplary cell 151, can be derived, at least in part, based on a comparison between the nucleotides, of the exemplary nucleotide sequences 110 and 120, that correspond to the exemplary cell 155, namely the nucleotide 121, from the exemplary nucleotide sequence 120, and the exemplary nucleotide 111, from the exemplary nucleotide sequence 110. If the aforementioned nucleotides 121 and 111, corresponding to the cell 151, match, then the cell can be assigned a score, or value, of "2". Conversely, if the nucleotides 121 and 111, corresponding to the cell 151, do not match, then a value of "−1" can be assigned, except that, according to one embodiment, the lowest score that can be assigned to any cell can be zero. Consequently, if the nucleotides 121 and 111, corresponding to the cell 151, do not match, then the cell 151 can be assigned a score of zero.

Subsequent cells of the exemplary matrix 100 can be generated in an analogous manner, except that they can also take into account the scores of previously generated cells. For example, and with reference to FIG. 1, an exemplary generation of a score 135, for the exemplary cell 155, is illustrated. More specifically, one aspect of the generation of the score 135, for the exemplary cell 155, is visually illustrated by the arrow 151, which can represent a determination of the score 135 that is based on the score 131, of the prior cell 141, in combination with a value indicative of whether or not the corresponding nucleotides, corresponding to the cell 151, namely the nucleotides 112 and 122, match one another. Such a value, indicative of whether the nucleotides 112 and 122 match, can be in accordance with the afore described valuing system, whereby a match is assigned a value of "2", whereas a mismatch is assigned a value of "−1". Thus, for example, if the score 131, of the exemplary cell 151, was "2", due to the exemplary nucleotides 111 and 121, corresponding to the exemplary cell 151, matching one another, then the score 135, of the exemplary cell 155, in accordance with the calculation represented by the arrow 141, can be "4", if the corresponding nucleotides 112 and 122 match, or can be "1" if the corresponding nucleotides 112 and 122 do not match one another. More specifically, if the corresponding nucleotides 112 and 122 match, a value of "2", representing such a match, can be added to the exemplary score 131, yielding a score of "4" as the exemplary score 135 of the exemplary cell 155. Conversely, if the corresponding nucleotides 112 and 122 do not match, a value of "−1", representing such a mismatch, can be added to the exemplary score 131, yielding a score of only "1" as the exemplary score 135 of the exemplary cell 155.

As indicated previously, the calculation represented by the arrow 141 can be but one portion, or one aspect, taken into account in generating a score, or value, for a cell, such as exemplary score 135 for the exemplary cell 155. Other aspects are visually represented in the exemplary matrix 100 by the arrows 142 and 143. The calculation represented by arrow 142 can be the application, or addition, of a value, sometimes referred to as a "gap-scoring factor" to the score 132 of the cell 152, or any prior cell in the column above cell 155. If any of the calculations represented by the arrow 142 are found to yield a greater value, then than value becomes the score 135 of the cell 155. Typically, when this vertical calculation 142 yields the greatest result, it can be considered to be a delineation of a "deletion", where a nucleotide, or a string of nucleotides, in nucleotide sequence 120 are not present in nucleotide sequence 110 to which the nucleotide sequence 120 is being compared.

A determination represented by the arrow 143 can be similar to that described above in relation to arrow 142, in that a "gap-scoring factor" can be applied, or added to, the score 134 of the cell 154, or any previous horizontal cells in the row prior to cell 155. If any of the calculations represented by the arrow 142 are found to yield a greatest value, the score 135, of the cell 155, can be set to that value. When this horizontal calculation 143 yields the greatest result it can be a delineation of an "insertion", where a nucleotide, or string of nucleotides, in the nucleotide sequence 110 are not present in the nucleotide sequence 120 being compared to the nucleotide sequence 110.

The generation of scores of other cells of the exemplary matrix 100 can proceed in a like manner. For example, the generation of the score 139, of the cell 159, can be based on the largest of: (1) the score of a horizontally prior cell as added to a corresponding gap scoring factor, (2) the score of a vertically prior cell as added to a corresponding gap scoring factor or (3) the score of a diagonally prior cell as combined with the aforementioned similarity function. Thus, within the context of the cell 159, vertically prior cells can include cells whose scores, or values, were previously generated and which are in a same column of the exemplary matrix 100 as the cell 159, or, stated differently, cells that correspond to a same nucleotide 113, of the nucleotide sequence 110, as the cell 159. Similarly, within the context of the cell 159, horizontally prior cells can include cells who scores, values, were previously generated and which are in the same row of the exemplary matrix 100 as the cell 159, or, stated differently, cells that correspond to a same nucleotide 123, of the nucleotide sequence 120, as the cell 159. Lastly, in terms of the cell 159, a diagonally prior cell can be the cell 155, which can also be referred to as a "diagonally immediately prior cell".

Given the terminology as defined above, one aspect of the generation of the score 139 of the cell 159 can be the score 135 of the diagonally immediately prior cell, namely the cell 155, as combined with the aforementioned similarity function, which can add "2" to the score 135 if the nucleotides corresponding to the cell 159, namely the nucleotides 123 and 113, match one another, or which can add "−1" to the score 135 if the corresponding nucleotides 123 and 113 not match.

Another aspect of the generation of the score 139 can be the scores of vertically prior cells as combined with the aforementioned gap-scoring factor. For example, the score 136 of the immediately vertically prior cell 156 can be added to a gap-scoring factor associated with cell 156 for purposes of generating the score 139 of the cell 159. As another example, the score 133, of the vertically prior cell 153, can be added to a gap-scoring factor associated with the cell 153. According to one aspect, the gap-scoring factor associated with the cell 153 can be the same as the gap-scoring factor associated with the cell 156. According to another aspect, the gap-scoring factor associated with the cell 153 can be different from the gap scoring factor associated with the cell 156. As will be recognized by those skilled in the art, the gap-scoring factor can be user-selected based on various user-specific requirements in comparing the two nucleotide strings or sequences, such as user-specific requirements reflective of how tolerant the comparison is to be with respect to one or more nucleotides that are present in one nucleotide sequence, but not in the other. To generate the score 139, of the cell 159, the score 136 of the immediately vertically prior cell 156 can be added to the gap-coring factor associated with cell 156. That sum can then be compared to the score 133, of the vertically prior cell 153, as added to the gap scoring factor associated with that cell, namely the cell 153, and the largest of those two sums can then represent the portion of the score 139 derived from vertically prior cells. That portion, derived from vertically prior cells, can then be compared with the portion derived from the diagonally immediately prior cell in the manner detailed above. Again, the larger of the two can be selected as the score 139 of the cell 159.

A third aspect of the generation of the score 139 can be the scores of horizontally prior cells which, like the aforementioned vertically prior cells, can be combined with gap-scoring factors. For example, the score 138 of the immediately horizontally prior cell 158 can be added to a gap-scoring factor associated with cell 158 for purposes of generating the score 139 of the cell 159. As another example, the score 137, of the horizontally prior cell 157, can be added to a gap-scoring factor associated with the cell 157. As before, the gap-scoring factor associated with the cell 157 can be the same as, or different from, the gap-scoring factor associated with the cell 158 based on various user-specific requirements in comparing the two nucleotide strings or sequences. To generate the score 139, of the cell 159, the score 138 of the immediately horizontally prior cell 158 can be added to the gap-coring factor associated with cell 158. That sum can then be compared to the score 137, of the horizontally prior cell 157, as added to the gap scoring factor associated with that cell, namely the cell 157, and the largest of those two sums can then represent the portion of the score 139 derived from horizontally prior cells. That portion, derived from horizontally prior cells, can then be compared with the portion derived from the vertically prior cells as well as the portion derived from the diagonally immediately prior cell in the manner detailed above. The larger can be selected as the score 139 of the cell 159.

Figure 2:
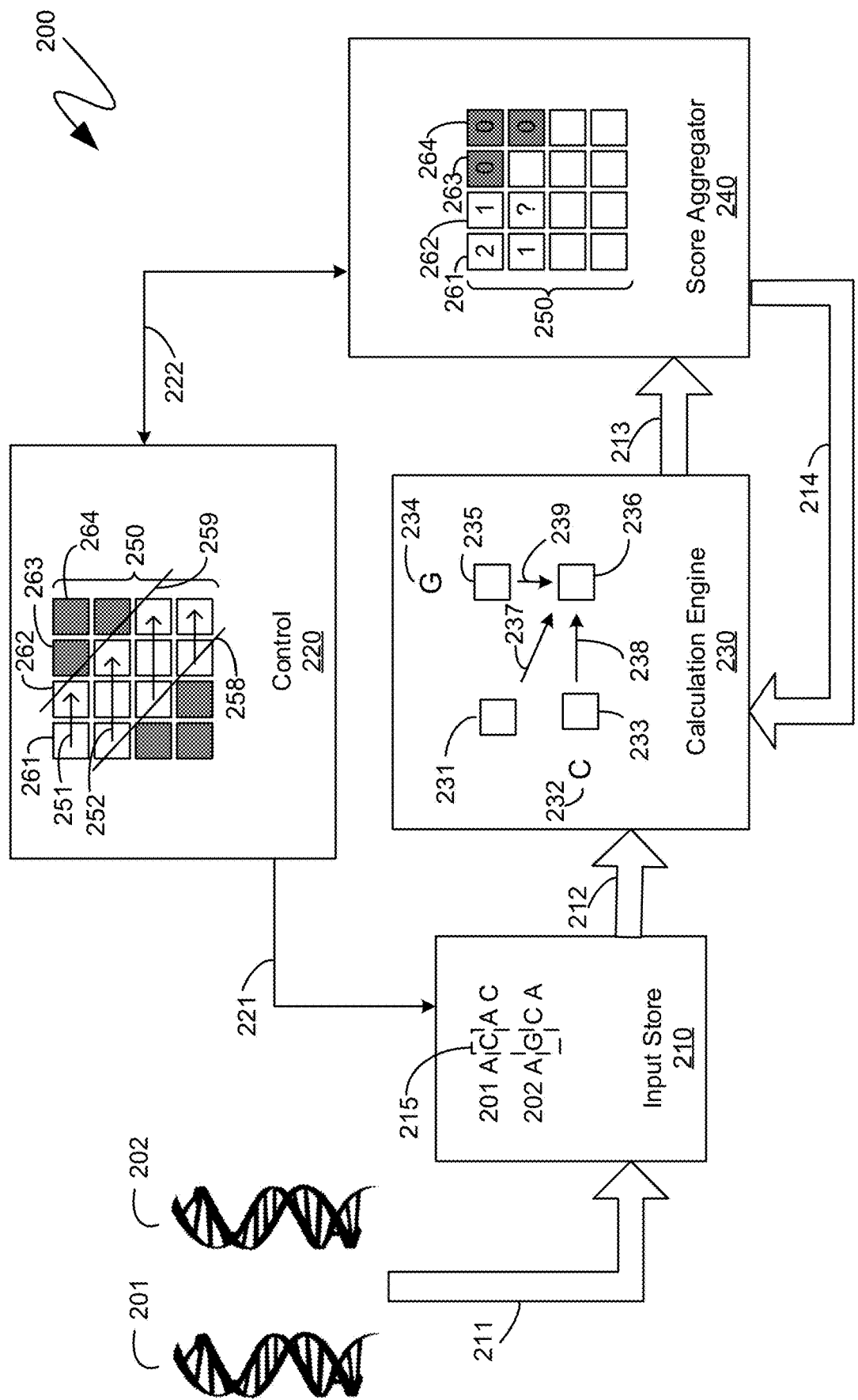
FIG. 2 is a block diagram of an exemplary customized integrated circuit for comparing two nucleotides in a sequential manner.

Turning to FIG. 2, the exemplary system 200 shown therein illustrates various components, or collections of integrated circuitry, which can, together, comprise a customized integrated circuit that can compare nucleotide sequences in a serial manner. Initially, two nucleotide sequences, such as exemplary nucleotide sequences 201 and 202 can be received as input and stored in an input store 210, as graphically represented by the arrow 211. The exemplary input store 210 can comprise integrated circuitry for the storage of digital data, such as in a manner well known to those skilled in the art. Additionally, while nucleotide sequences 201 and 202 are graphically represented by a double helix, those of skill in the art will recognize that typically only one half of such a double helix will be utilized for purposes of nucleotide sequence comparisons. The nucleotide sequences being compared, such as exemplary nucleotide sequences 201 and 202, can be obtained through any of a variety of means, typically involving specialized hardware for the extraction of genetic material.

In addition to storing the nucleotide sequences being compared, the input store 210 can also store various user settings or user input relevant to the comparison of the two nucleotide sequences. For example, as described in detail above, a gap-scoring factor can be a variable whose value can be based on various user-specific requirements in comparing the two nucleotide strings. Consequently, one or more gap-scoring factors can be specified, either directly by a user, or can be derived based upon other user input, and such gap-scoring factors can be stored, in the form of digital data, in the circuitry comprising the input store 210. When such gap-scoring factors are then to be utilized by the calculation engine 230, to generate a score for a cell selected by the control unit 220, the relevant gap-scoring factors can be among the data provided to the calculation engine 230, by the input store 210, such as is graphically represented by the arrow 212.

A calculation engine, such as the exemplary calculation engine 230, can comprise integrated circuitry that can facilitate the performance of the above-described generation of scores for individual cells in a two-dimensional matrix whose dimensions are defined by the nucleotides, of the nucleotide sequences 201 and 202, as stored in the input store 210. As detailed above, the generation of a score for an individual cell of a two-dimensional matrix, such as the exemplary cell 236, can be the largest value as among: (1) the scores of one or more horizontally prior cells, such as the exemplary horizontally prior cell 233, (2) the scores of one or more vertically prior cells, such as the exemplary vertically prior cell 235, or (3) the score of a diagonally prior cell, such as the exemplary diagonally prior cell 231, as summed to a value that is dependent upon whether or not the nucleotides corresponding to the exemplary cell 236, such as the exemplary nucleotides 232 and 234, match one another. The arrows 238, 239 and 237, respectively, signify the three values, the largest of which can be selected as the score of the exemplary cell 236.

The operation of the calculation engine 230 can be controlled by a control component, such as the exemplary control unit 220. The exemplary control components 220 can comprise integrated circuitry that can facilitate the selection of a nucleotide, from the nucleotide sequence 201, and a corresponding nucleotide, from the nucleotide sequence 202, as stored in the input store 210, and can then further facilitate the provision of such a corresponding pair 215 of nucleotides to the calculation engine 230 for purposes of generating a score for a cell, such as exemplary cell 236. The selection of the pair 215 of nucleotides, from the nucleotide sequences 201 and 202, as stored in the input store 210, is graphically represented by the arrow 221. Such a pair 215 of nucleotides can then be provided to the calculation engine 230, by the control unit 220, as graphically represented by the arrow 212. Once the calculation engine 230 has completed generating a score for a selected cell, such as the exemplary cell 236, such a score, and the cell to which it applies, can be communicated to a score aggregator unit, such as the exemplary score aggregator unit 240.

According to one aspect, the score aggregator unit 240 can comprise integrated circuitry that can facilitate the storage of digital data representative of a two-dimensional matrix, such as the exemplary two-dimensional matrix 250 shown in FIG. 2. As such, the score aggregator unit 240 can receive scores of individual cells from the calculation engine 230, as illustrated by the arrow 213, and, can thereby retain the scores of the individual cells of the two-dimensional matrix 250. As will be recognized by those skilled in the art, the scores of the individual cells of the two-dimensional matrix 250 can enable backtracking, or other like mechanisms, to further analyze the similarity between the nucleotide sequences 201 and 202. According to another aspect, the score aggregator unit 240 can retain additional information about the matrix 250 or individual cells thereof. For example, the score aggregator unit 240 can maintain a continuously updated value reflective of the highest score generated for a cell thus far by the calculation engine 230. Additionally, the score aggregator unit 240 can maintain the indices, or coordinates, within the two-dimensional matrix 250, of the cell whose score is currently the highest score. As another example, the score aggregator unit 240 can maintain the second-highest score, and coordinates of the corresponding cell.

As indicated previously, the control unit 220 can control the operation of the calculation engine 230. One aspect of the functionality of the control unit 220 can be the selection of a cell of the two-dimensional matrix for which the calculation engine 230 is to generate a score. Upon selection of a cell, the control unit 220 can further provide, to the calculation engine 230, the relevant inputs to enable the calculation engine 230 to generate a score for the selected cell. For example, the control unit 220 can provide, to the calculation engine 230, a nucleotide from the first nucleotide 201 and a nucleotide from the second nucleotide 202 that correspond to the selected cell. Such a corresponding pair of nucleotides can be utilized by the calculation engine 230, as detailed above, to generate a score for the selected cell. In addition to the aforementioned corresponding pair of nucleotides, such as the exemplary corresponding pair of nucleotides 215, the control unit 220 can further provide the scores, previously generated by the calculation engine 230, or otherwise obtained, of prior cells of the two-dimensional matrix 250. Such scores of prior cells of the two-dimensional matrix can be utilized, such as in the manner detailed previously, by the calculation engine 230 to generate a score of the cell selected by the control unit 220. The scores of prior cells of the two-dimensional matrix can be obtained by the control unit 220 from the score aggregator 240, as illustrated by the arrow 222. Alternatively, or in addition, the control unit 220 can maintain, or can cause to be maintained by other components, such as the exemplary calculation engine 230, a cache of previously generated scores of prior cells of the two-dimensional matrix. According to one aspect, such a cache can comprise a quantity of scores that is one greater than a quantity of cells in a row of the two-dimensional matrix, such as exemplary two-dimensional matrix 250.

Figure 3:
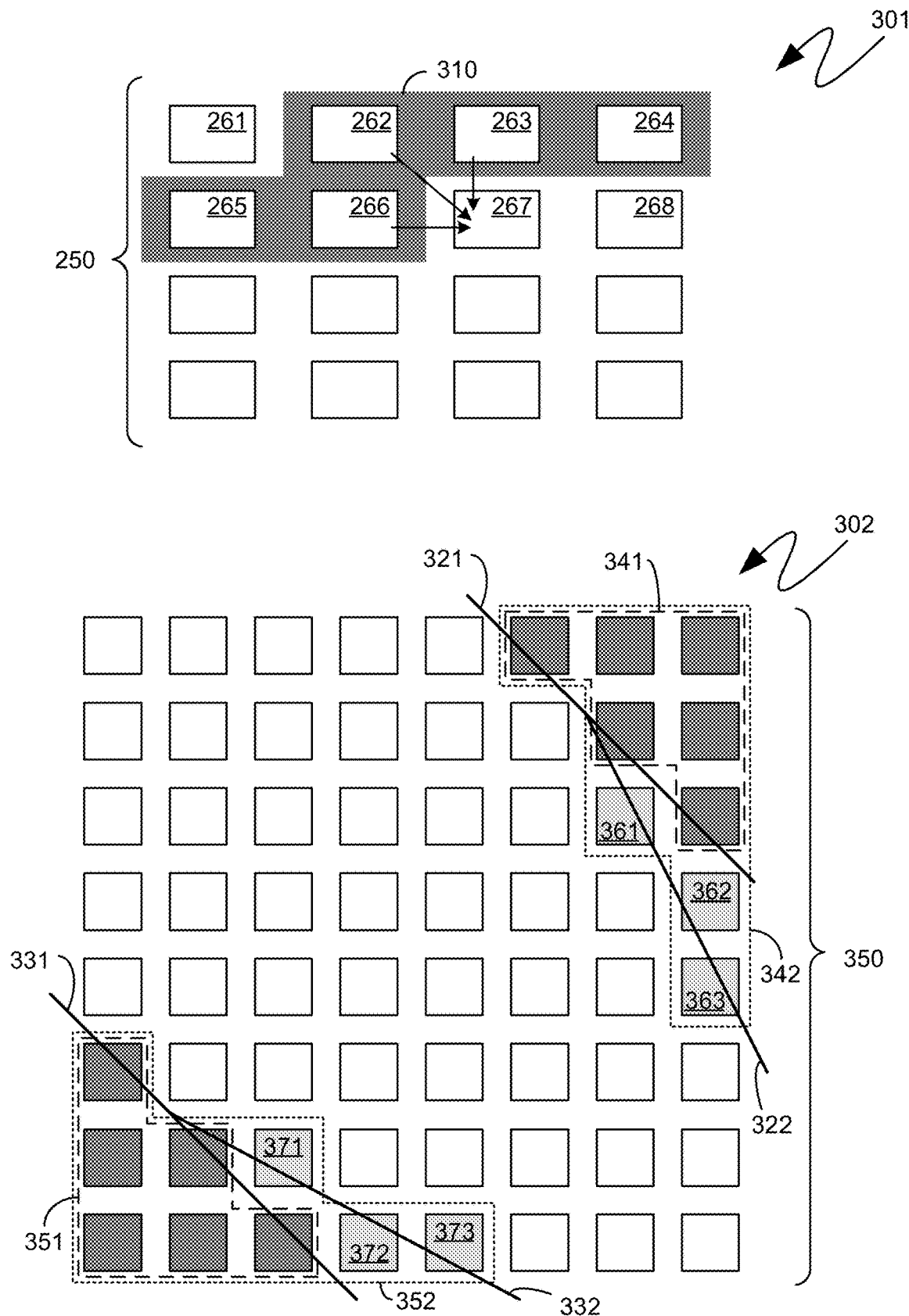
FIG. 3 is a block diagram of an aspect of an exemplary customized integrated circuit for comparing two nucleotides in a sequential manner.

For example, turning to FIG. 3, the exemplary system 301 illustrates exemplary two-dimensional matrix 250 referenced in FIG. 2, except showing a collection of cells 310 whose values can be cached so that values of prior cells, relevant to the generation of a value of a selected cell, can be efficiently provided to the calculation engine 230. For example, in the exemplary system 301, the cell 267 can have been selected by the control unit 220, shown in FIG. 2, to have its score generated by the calculation engine 230, also shown in FIG. 2. As detailed previously, the generation of a score for the cell 267 can take into account the scores assigned to the cells 262, 263 and 266, as illustrated by the arrows in FIG. 3. Thus, a collection of cells 310 whose values can be cached can include the cells 262, 263 and 266. Typically, the values of prior cells can be determined in a consecutive manner, proceeding in a left-to-right, and top-to-bottom, manner. Thus, for example, a score for the cell 261 can have been generated, followed by the selection of cell 262, for which a score can then be generated, thereafter continuing a generating the score of the cell 263, then the cell 264, then the cell 265, and so on. In such an instance, the cells whose scores are cached can be the immediately previously selected cells, with the quantity of such cells whose scores are cached being one greater than the quantity of cells in a row of the two-dimensional matrix.

As illustrated by the system 301 of FIG. 3, in the simple exemplary two-dimensional matrix 250, which comprises only four columns, or four cells in each row, the quantity of cells whose scores were immediately previously generated can be five, or one greater than the quantity of cells in each row. Such a cache allows the score of the cell 262, for example, to continue to be cached when the cell 267 is selected to have its score generated. Consequently, such a cache would include the scores of the cells 262, 263 and 266, which can all be utilized, as illustrated by the arrows of FIG. 3, in the generation of the score of the selected cell 267. Once the score of the cell 267 is generated, the score of the cell 262 can no longer be retained in the cache, and, instead, the cache can be updated to retain the values of the five cells who scores were immediately previously generated, namely, in the present example, the cells 263, 264, 265, 266 and 267. Consequently, when the cell 268 is subsequently selected to have its score generated, the cache can then include the cells 263, 264 and 267 who scores could be utilized in the generation of the score of the cell 268. The caching can proceed in a like manner as subsequent cells of the exemplary two-dimensional matrix 250 are selected and their scores generated.

Returning to FIG. 2, as indicated previously, the control unit 220 can select which cell, of the two-dimensional matrix 250, is next to have a score generated for it by the calculation engine 230. According to one aspect, the control unit 220 can select cells of the two-dimensional matrix 250 in a linear, sequential manner commencing with a cell at the upper left of the matrix such as, for example, the cell 261 shown in FIG. 2. Subsequently, while the score for the cell 261 is being generated by the calculation engine 230, or after the completion of such a score generation action, the control unit 220 can select a subsequent cell, such as the exemplary cell 262. In such a manner, the control unit 220 can proceed linearly down a row of the two-dimensional matrix 250, such as is visually illustrated by the arrow 251. Upon reaching the end of a row of the two-dimensional matrix 250, according to one aspect, the control unit 220 can proceed to the next lower row and, again, select individual cells in a linearly sequential manner proceeding down that next lower row from the leftmost cell of that row to the rightmost cell of that row, such as in the manner illustrated by the arrow 252.

According to one aspect, there may be certain cells of the two-dimensional matrix that the control unit 220 can determine to not instruct the calculation engine 230 to generate a score for such cells, but, instead, the control unit 220, either by itself, or in combination with, for example, the calculation engine 230, can cause those cells to simply be assigned a score of zero. One mechanism by which a two-dimensional matrix, such as that whose cells are having their scores generated by the system 200, can be utilized to evaluate the similarity between two sequences of nucleotides can be based on a backtracking that can be performed through the two-dimensional matrix once values, or scores, for the cells of the two-dimensional matrix have been determined. As will be recognized by those skilled in the art, such a backtracking typically commences at the bottom right of a two-dimensional matrix and proceeds in an approximately diagonal manner towards the upper left of the two-dimensional matrix. Consequently, cells located in the upper right or lower left of the two-dimensional matrix are typically not utilized as part of the backtracking.

According to one aspect, therefore, the control unit 220 can choose to skip the determination of scores for cells whose scores are not likely to be useful in comparing a pair of nucleotide sequences, such as, for example, those cells located in the upper right or lower left of the two-dimensional matrix. More specifically, thresholds, such as the exemplary thresholds 258 and 259 can demarcate between cells of the two-dimensional matrix 250 for which values are to be generated and cells of the two-dimensional matrix 250 for which the generation of a score, such as in the manner detailed above, and such as would be performed by the calculation engine 230, can be skipped, and, instead, a value of zero can simply be entered as the score of such a cell.

Because the mechanisms described herein determine the scores of individual cells of the two-dimensional matrix 250 in a serial, rather than parallel, manner, skipping the generation of a score for one or more cells can result in a performance improvement. By contrast, in typical implementations of, for example, the Smith-Waterman algorithm on customized integrated circuitry, the generation of a score for each cell among a collection of cells typically oriented in a diagonal across the matrix from lower-left to upper-right (also termed an "anti-diagonal" in the art) is performed in parallel such that, in one cycle, the score for each and every cell in that collection of cells is generated. In such a typical implementation, therefore, there is no performance improvement in skipping the generation of scores for one or more cells because the remaining cells in the anti-diagonal will still need their scores generated and, so long as there is at least one cell in the anti-diagonal whose score needs to be generated, the generation of the scores of those cells will still take the same amount of time as if all of the cells in the anti-diagonal needed to have their scores generated.

To determine whether a selected cell is to have its score generated by the calculation engine 230, the control unit 220 can reference a predetermined threshold, such as the exemplary thresholds 258 and 259, that can demarcate between cells of the two-dimensional matrix 250 for which values are to be generated, such as, for example, the cells 261 and 262, and cells of the two-dimensional matrix 250 for which scores need not be generated, such as the exemplary cells 263 and 264. Thus, for example, when the control unit selects the cell 262, after its selection of the cell 261 and the generation of the score thereof by the calculation engine 230, the control unit 220 can reference the predetermined threshold 259 in order to determine whether the selected cell 262 is to have its score generated by the calculation engine 230. Since the selected cell 262 is on the side of the threshold 259 as the other cells whose scores are to be generated, the control unit 220 can provide the relevant inputs to the calculation engine 230 to enable the calculation engine 230 to generate the score of the selected cell 262. Subsequently, the control unit 220 can reference the threshold 259 to determine whether the next selected cell, namely the cell 263, is to have a score generated for it. Because the cell 263 can be determined to be on an opposite side of the threshold 259, the control unit 220 can determine the cell 263 to be part of the collection of cells whose scores are not to be determined, and, consequently, the control unit 220 can either provide, such as directly to the score aggregator 240, a value of zero for the score of the selected cell 263, or the control unit 220 can instruct the calculation engine 23 to not generate a score for the selected cell 263 and, instead, assign it a score of zero, which can then be provided to the score aggregator 240, such as illustrated by the arrow 213. In a similar manner, the control unit 220 can determine that the cell 264 is part of the cells that are demarcated by the threshold 259 as cells for which scores need not be generated and, again, can cause a score of zero to be assigned to such a cell. In such a manner, the generation of the scores for at least some of the cells of the matrix 250, such as those cells shown shaded in gray in FIG. 2, such as the exemplary cells 263 and 264, can be skipped, and a performance improvement can be achieved thereby since, as will be recognized by those skilled in the art, the assignment of a value of zero can be substantially faster than the actual generation of a score, such as by the calculation engine 230 in accordance with the mechanisms detailed above.

The thresholds that demarcate between cells whose scores are to be generated by the calculation engine 230, and cells whose scores are not to be generated by the calculation engine 230 and, instead, are simply to be set to zero, such thresholds can be oriented in a diagonal manner across the two-dimensional matrix, such as the exemplary two-dimensional matrix 250, such as in the manner illustrated by the exemplary thresholds 258 and 259 shown in FIG. 2. When oriented in a diagonal manner across the two-dimensional matrix, a threshold can demarcate between cells located in a corner of the matrix, such as cells located in an upper right corner, and cells located towards the center of the matrix. As indicated previously, it can be determined that cells in the upper right corner, and lower left corner, of a two-dimensional matrix can be of marginal value in comparing two nucleotide sequences. More specifically, the two nucleotide sequences that are being compared are often very similar and, since a perfectly matching pair of nucleotide sequences would have the best scores lie exactly along the diagonal, closely matching sequences will have a path to the best score that lies very close to the diagonal, and, therefore, cells further away from the diagonal towards the upper right and lower left corners can be less useful and their scores can be, essentially, ignored, without meaningful negative impact on the overall accuracy of the comparison. Consequently, according to one aspect, two approximately parallel thresholds can be established demarcating between one set of cells, in between the two thresholds, whose scores are to be generated by the calculation engine 230, and two other sets of cells, one in the upper right corner of the matrix, and another in the lower left corner of the matrix, whose scores are not to be generated by the calculation engine 230 and, instead, are simply to be assigned scores of zero. Additionally, the threshold, demarcating between cells whose values are to be generated by the calculation engine 230, and cells which are to be assigned a value of zero, can demarcate between two contiguous groupings of cells such that cells whose values are to be generated by the calculation engine are contiguous with one another and are bounded by the boundaries of the two dimensional matrix and the threshold, while the cells whose values are not to be generated by the calculation engine are, similarly, contiguous with one another and are bounded by the boundaries of the two-dimensional matrix and the threshold, such as in the manner illustrated by the white and shaded cells of the exemplary matrix 250 shown in FIG. 2.

The thresholds that demarcate between cells who scores are to be generated, and the cells whose scores are not to be generated and, instead, are to be assigned a score of zero, such thresholds can be directly established by user input. Alternatively, such thresholds can be derived from indirect user input, such as user input selecting between a more accurate comparison of two nucleotide sequences that requires a greater amount of time to generate, and a less accurate comparison of the two nucleotide sequences that can be generated more quickly, such as by excluding cells of the two-dimensional matrix from having their scores generated by the calculation engine 230 in accordance with specified thresholds, such as in the manner detailed above. Such thresholds, whether directly specified by the user, or whether generated based on indirect user input, can be stored in the input store 210 and obtained by the control unit 220 therefrom. Alternatively, or in addition, such thresholds can be maintained by the control unit 220 directly.

While illustrated as straight lines, thresholds demarcating between cells whose scores are to be generated and cells who scores are not to be generated can be conceptualized, or visualized, as the combination of lines of differing angles. For example, and with reference to the exemplary system 302 shown in FIG. 3, a first threshold, such as the exemplary threshold 321, can demarcate between a first set of cells 341, who scores are not to be generated, and a second set of cells who scores are to be generated. A second threshold, such as exemplary threshold 322, can slice through the two-dimensional matrix 350 at an angle differing from the angle at which the first threshold 321 sliced through the two-dimensional matrix 350. Consequently, as a result of the exemplary threshold 322, additional cells, such as the exemplary cells 361, 362 and 363, can be added to the set of cells whose scores are not to be generated. Stated differently, the additional threshold 322 can expand the set of cells 341, whose scores are not to be generated, into a larger set of cells 342 encompassing additional cells, such as the exemplary cells 361, 362 and 363.

The exemplary system 302 illustrates a corresponding set of thresholds 331 and 332 which, like the aforementioned thresholds 321 and 322, demarcate between a set of cells whose scores are to be generated and a set of cells, namely the set of cells 351, subsequently expanded into the set of cells 352 by the addition of the threshold 332, whose scores are not to be generated. As can be visually perceived from the exemplary system 302 shown in FIG. 3, the combined result of the additional thresholds 322 and 332 is to further "envelope", or narrow down, the quantity of cells whose scores are to be generated as proceeding from the upper left of the exemplary two-dimensional matrix 350 and continuing down towards the lower right of that matrix.

Although illustrated in the exemplary system 302, shown in FIG. 3, as increasing the quantity of cells whose scores are not to be generated, additional thresholds, or thresholds oriented at different angles with respect to other thresholds, can, likewise, subtract cells from the quantity of cells whose scores are not to be generated, thereby "widening out", rather than "enveloping", the cells whose scores are to be generated. In another aspect, this thresholding can also be dynamically determined, or modified, based on previously generated scores of prior cells. For example, it can be dynamically determined that some cells of the two-dimensional matrix will likely have scores that are too low to be relevant and, consequently, thresholds can be dynamically established, or modified, to skip calculation for these cells. For example, if the first or last cell in a row has a score generated for it that is zero, then such a generated score can inform the dynamic determination or modification of thresholds demarcating those cells whose scores need not be generated.

In yet another aspect, thresholds can be established that demarcate among individual cells, or discontiguous groupings of cells, and those of skill in the art will recognize that the mechanisms detailed herein are not limited to linear thresholds, or simple thresholds merely dividing the two-dimensional matrix into two contiguous groupings of cells.

Turning back to FIG. 2, the aforedescribed input store 210, control unit 220, calculation engine 230 and score aggregator 240 can be implemented in customized integrated circuitry in a manner well known to those skilled in the art. For example, within the well-known, and above described, FPGA context, an FPGA can have a series of gates oriented such that the application of electrical signals and voltages to specific input terminals of specific gates can cause the FPGA to, for example, implement the functionality detailed above with respect to the control unit 220, the calculation engine 230, and so on.

According to one aspect, multiple control units, such as the exemplary control unit 220, can share a single calculation engine, such as exemplary calculation engine 230. Such an arrangement can enable optimal physical positioning of the integrated circuitry implementing such control units with respect to the physical location of the integrated circuitry implementing the calculation engine such that the distance between them is reduced, thereby enabling such customized integrated circuitry to operate at a higher clock frequency and with less time between processing cycles.

Figure 4:
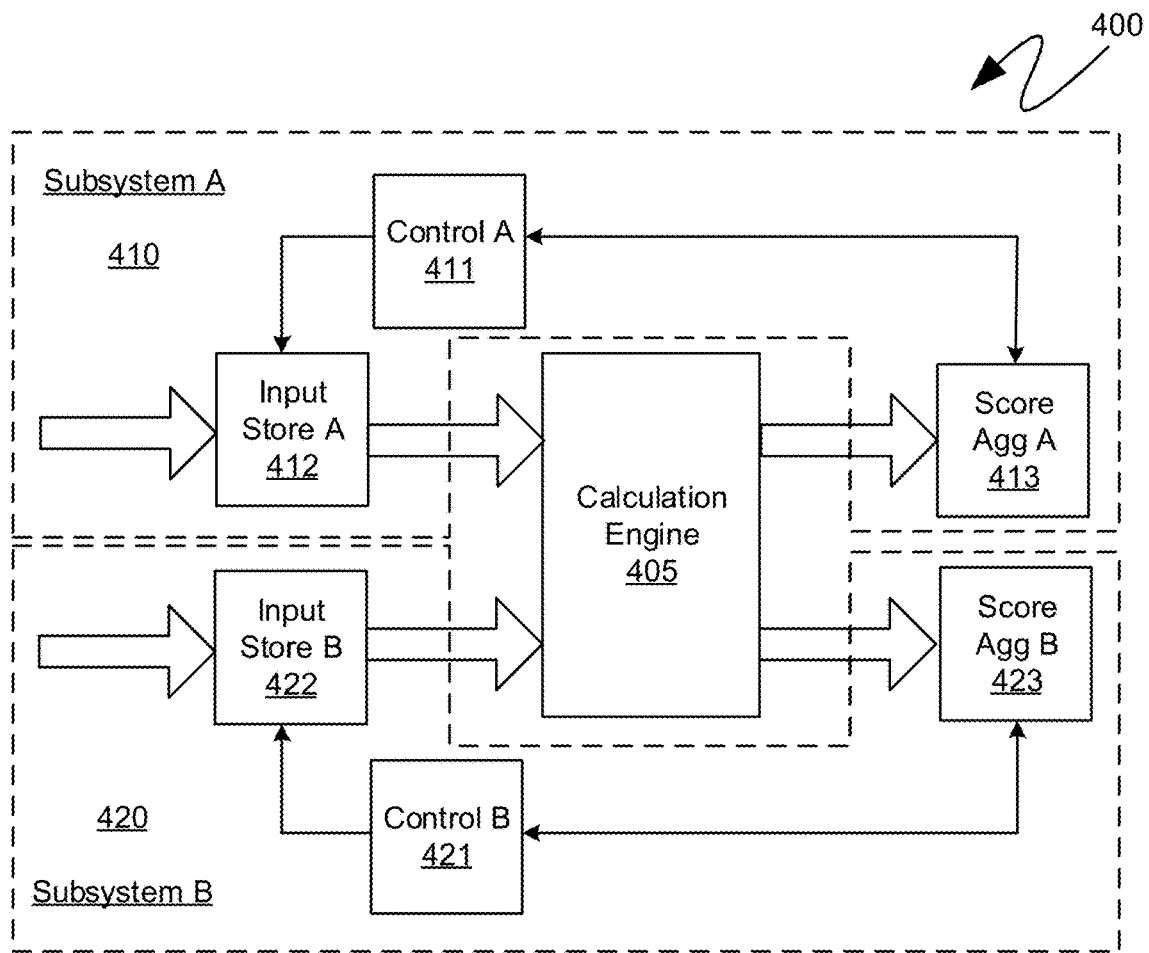
FIG. 4 is a block diagram of another exemplary customized integrated circuit for comparing two nucleotides in a serialized manner.
Figure 4:
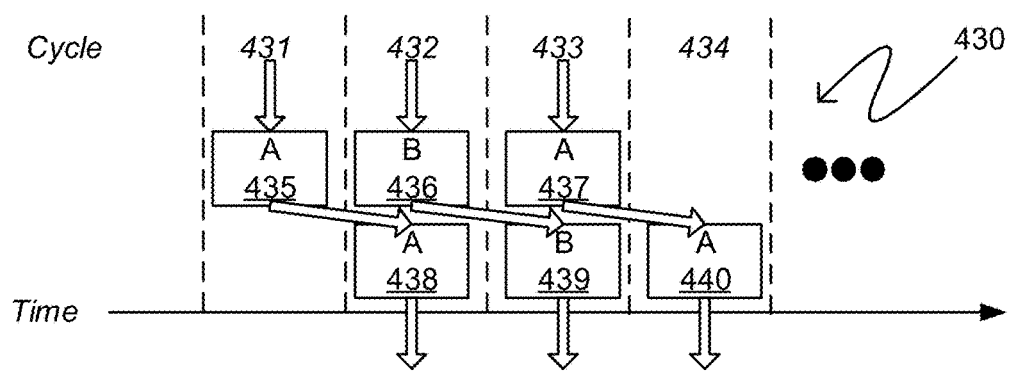
Figure 4:
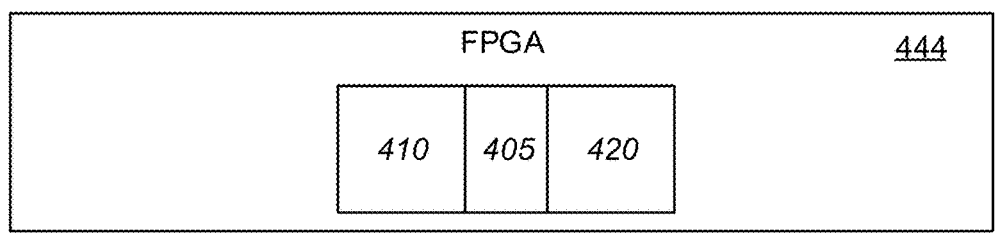

Turning to FIG. 4, the exemplary system 400 shown therein illustrates an exemplary utilization of the single calculation engine, namely the exemplary calculation engine 405, by multiple different subsystems, such as the exemplary subsystems 410 and 420, each comprising control units, score aggregation components, and input stores, that are separate and independent of one another. Thus, for example, the subsystem 410, comprising the control unit 411, the input store component 412 and the score aggregation component 413 can utilize the calculation engine 405 in comparing one pair of nucleotide sequences, while the subsystem 420, comprising the control unit 421, the input store component 422 and the score aggregation component 423, can utilize the same calculation engine 405 to compare another, different pair of nucleotide sequences. With the exception of the sharing of the calculation engine 405, the components of the subsystems 410 and 420, and the calculation engine 405 itself, can operate in the same manner as that described in detail above with respect to the system 200 shown in FIG. 2.

According to one aspect, to facilitate sharing of the calculation engine 405, the calculation engine 405 can alternate between the generation of scores for cells selected by the control unit 411 of the subsystem 410, and the control unit 421 of the subsystem 420. More specifically, and as will be detailed further below, the operations of the calculation engine 405, and the corresponding circuitry performing such operations, can be subdivided such that a portion of the operations, performed by a portion of the circuitry, can be completed and the intermediate results then passed to another portion that can, for example, complete the operations of the calculation engine 405. The exemplary temporal illustration 430 visually indicates how such an alternating processing through different subportions of the calculation engine's circuitry can be implemented. For purposes of the present example, graphically illustrated by the temporal diagram 430 the processing performed by the calculation engine 405 can be divided into two halves, each of which can complete the portion of the processing being performed by such a half in one cycle, such as exemplary cycles 431, 432, 433 and 434, shown in the temporal diagram 430. An input, such as, for example, from the subsystem 410, can be received during cycle 431, and a portion of the processing performed by the calculation engine 405 can be performed during cycle 431, as represented by the chunk 435. A subsequent portion of the processing performed by the calculation engine 405 can then be performed during a subsequent cycle, namely cycle 432, as represented by the chunk 438, and the results thereof can be output during the cycle 432. From the perspective of the subsystem 410, the calculation engine 405 took two cycles, namely the cycles 431 and 432, to generate output.

However, by dividing the calculation engine 405 into portions, one or more other subsystems such as, for example, the subsystem 420, can utilize the calculation engine 405 during the same time periods. More specifically, once a first portion of the calculation engine 405 completes processing the chunk 435, during cycle 431, and passes those intermediate results onto another, different portion of the calculation engine to continue processing, such as the processing of chunk 438 during cycle 432, that first portion of the calculation engine becomes dormant and is available to perform other useful work. Thus, for example, while the second portion of the calculation engine is processing the chunk 438 during cycle 432, the first portion of the calculation engine can receive input from the subsystem 420 and can process, for example, the chunk 436 during that same cycle 432. Then, the first portion of the calculation engine 405 can complete the processing of chunk 436 in parallel with the second portion of the calculation engine 405 completing the processing of the chunk 438. The first portion of the calculation engine 405 can then pass the intermediate outputs of the chunk 436 on to the second portion of the coagulation engine, which can continue the processing of the calculation engine in the form of the chunk 439 during a subsequent cycle 433. Again, the first portion of the calculation engine can then be free to perform other useful work, such as the processing of the chunk 437 received from the subsystem 410. In such a manner, by dividing the calculation engine 405 up into discrete components that perform only a portion of the computations of the calculation engine, the alternating processing from multiple subsystems, such as exemplary subsystems 410 and 420, in a pipelined manner can be achieved.

Moreover, because each subportion of the calculation engine 405 is performing only a portion of the work of the overall calculation engine 405, its performance of such a portion of the work can be completed more quickly. Consequently, the duration of the individual cycles, such as the exemplary cycles 431, 432, 433 and 434 can be reduced. Or, stated differently, the processor frequency can be increased. Such pipelining and increased processor frequency can result in greater throughput per unit time.

In addition to providing for more efficient utilization of a calculation engine, such as by decreasing, or eliminating, "downtime" during which portions of a calculation engine are not performing useful work, another benefit to pairing multiple subsystems, such as the exemplary subsystems 410 and 420, with a single calculation engine that is divided into portions, such as the calculation engine 405, can be the physical location of the customized integrated circuitry implementing such subsystems with respect to the physical location of the customized integrated circuitry implementing the calculation engine, such as on an FPGA chip. For example, FIG. 4 illustrates an exemplary portion of an FPGA chip 444 that can have etched thereon silicon structures in the form of gates, and other like integrated circuitry, that can implement the calculation engine 405, as well as the exemplary subsystems 410 and 420. As shown in FIG. 4, the physical structures of the integrated circuitry that implements the calculation engine 405 can be physically positioned between the physical structures of the integrated circuitry that implements the exemplary subsystem 410 and the physical structures of the integrated circuitry that implements the exemplary subsystem 420 such that the physical distance, on the FPGA chip 444, between the exemplary subsystem 410 and the calculation engine 405, as well as the physical distance between the exemplary subsystem 420 and the calculation engine 405 is reduced. By reducing that physical distance, the speed with which electrical exchanges can be achieved can be increased, thereby enabling the computational frequency of, for example, the FPGA 444 to be increased. Stated differently, the reduction in the physical distance between the exemplary subsystems 410 and 420, respectively, and the calculation engine 405, can result in a reduction in the duration of each cycle, such as the cycles illustrated in the temporal diagram 430, thereby enabling the FPGA 444 to perform a greater quantity of useful work during a unit of time.

An additional benefit of sharing a single calculation engine, such as the calculation engine 405, among multiple subsystems, such as the exemplary subsystems 410 and 420, is that each of the subsystems can analyze and compare a unique pair of nucleotide sequences. For example, within the exemplary system 400 shown in FIG. 4, the exemplary subsystem 410 can compare a first pair of nucleotide sequences, while, at the same time, the exemplary subsystem 420 can compare a second, different pair of nucleotide sequences. As will be recognized by those skilled in the art, often multiple pairs of nucleotide sequences are to be compared as part of a single genetic project. Consequently, according to one aspect, customized integrated circuitry can include a dispatching unit that can receive multiple such pairs of nucleotide sequences and assign discrete pairs to individual subsystems, such as, for example, by assigning a first pair of nucleotide sequences to the subsystem 410 to be compared to thereby, and assigning a second, different pair of nucleotide sequences to the subsystem 420 to be compared thereby. In such a manner, the exemplary system 400 can compare two pairs of nucleotide sequences in a parallel, with each comparison proceeding in series, with the attendant benefits detailed above.

A single FPGA chip, or ASIC, for example, can comprise multiple systems such as the exemplary system 400. Moreover, while the exemplary system 400 illustrates only two subsystems sharing a single calculation engine, three or more subsystems can, likewise, share a single calculation engine. Consequently, a single chip can comprise multiple calculation engines, and each calculation engine can have associated therewith multiple independent subsystems, each of which can be assigned a unique pair of nucleotide sequences to compare, such as by the aforementioned dispatching unit. Because nucleotide sequences can be of varying lengths, the comparison of a shorter pair of nucleotide sequences can be performed more quickly in the comparison of the longer pair of nucleotide sequences. Consequently, according to one aspect, the dispatching unit can assign, to each pair of nucleotide sequences to be compared to one another, a unique identifier. Subsequently, as the subsystems to which such nucleotide sequences were assigned complete their comparison thereof, the dispatching unit can reorder the results in accordance with the unique identifiers. The overall output, therefore, can be presented, such as to a user, in the same order as the pairs of nucleotide sequences were provided as input.

Figure 5:
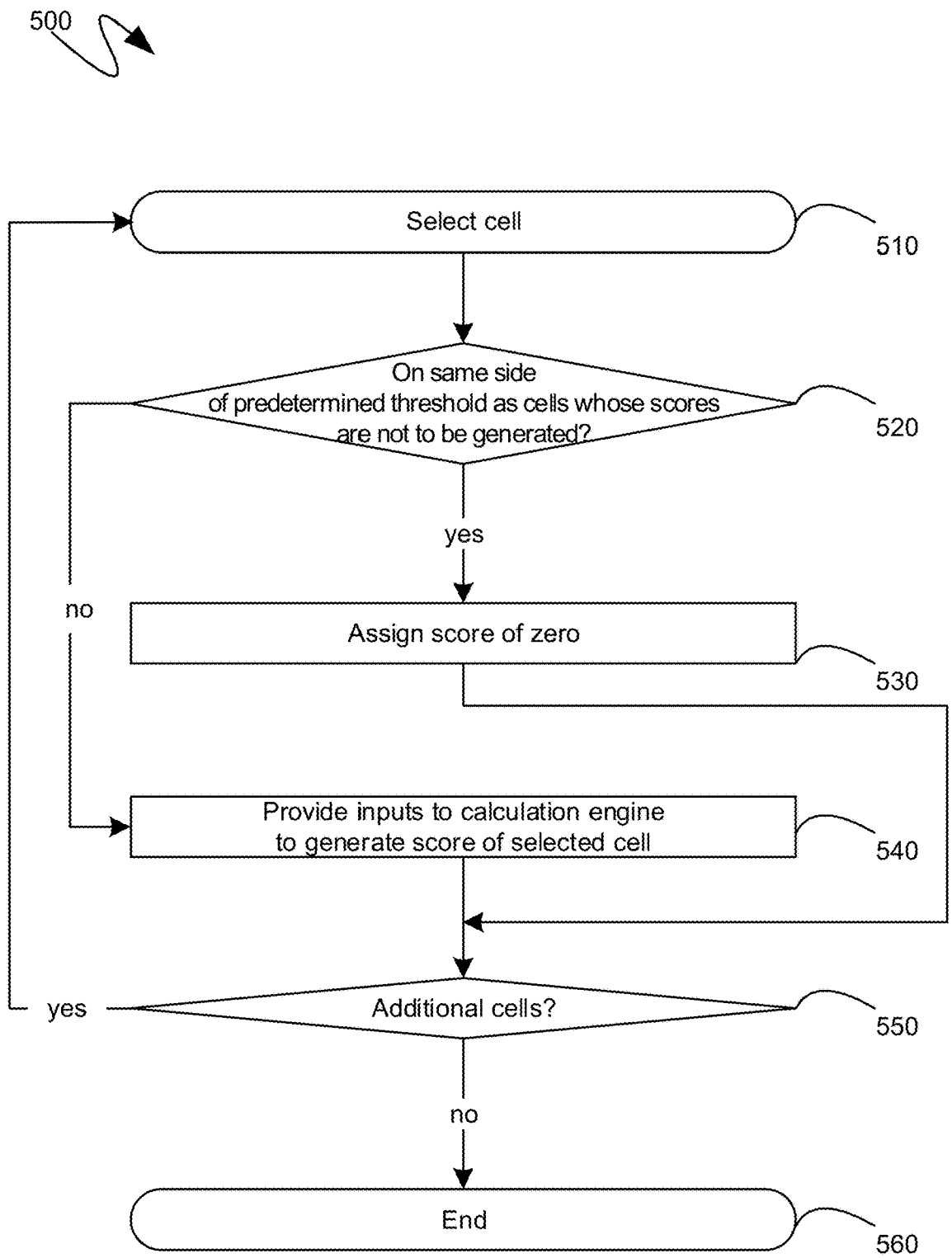
FIG. 5 is a flow diagram of the operation of an exemplary customized integrated circuit for comparing two nucleotides in a sequential manner.

Turning to FIG. 5, the exemplary flow diagram 500 shown therein illustrates an exemplary series of steps that can be performed by a control unit, such as the exemplary control units described in detail above. Initially, at step 510, a cell of a two-dimensional matrix can be selected. As detailed previously such a selection can be based on a linear, sequential processing of cells of a two-dimensional matrix. Subsequently, at step 520, the selected cell can be compared with one or more predetermined thresholds, which, as detailed above, can demarcate between cells whose scores are to be generated and cells whose scores and need not be generated and which can, instead, simply be assigned a score of zero. Based on the determination at step 520, processing can proceed to step 530, if the determination is made that the cell, selected at step 510, is on a same side of a predetermined threshold as cells whose scores are not to be generated. At step 530, therefore, the cell, selected in step 510, can be assigned a score of zero, and processing can proceed to step 550. Conversely, if, at step 520, a determination was made that the cell, selected at step 510, is on a side of a predetermined threshold as cells whose scores are to be generated, then processing can proceed to step 540. At step 540, the relevant inputs can be provided to a calculation engine, such as in the manner detailed above, to generate a score of the cell selected at step 510. Processing can then proceed to step 550. At step 550, a check can be made as to whether there are additional cells of the two-dimensional matrix that have not yet been selected. If, based in the determination, at step 550, there are such additional cells, processing and return to step 510 to select a subsequent cell. Alternatively, the relevant processing can end at step 560.

While described within the context of customized integrated circuitry, such as on an FPGA chip or ASIC, the mechanisms described can, likewise, be implemented by a computing device that can either comprise such customized integrated circuitry, or which can perform the aforedescribed steps on a conventional general-purpose processing unit. Consequently, turning to FIG. 6, an exemplary computing device 600 is shown therein comprising one or more general-purpose processing units, such as the exemplary CPU 620, an exemplary customized integrated circuit 650, as well as a system memory 630, and a system bus 621 that couples various system components including the system memory to the processing unit 620 and the customized integrated circuit 650. The system bus 621 may be any of several types of bus structures including a memory bus or memory controller, a peripheral bus, and a local bus using any of a variety of bus architectures. Depending on the specific physical implementation, one or more of the CPUs 620, the customized integrated circuit 650, the system memory 630 and other components of the computing device 600 can be physically co-located, such as on a single chip or silicon die or on a single circuit board. In such a case, some or all of the system bus 621 can be nothing more than silicon pathways within a single chip structure or on a single die and its illustration in FIG. 6 can be nothing more than notational convenience for the purpose of illustration.

The computing device 600 also typically includes computer readable media, which can include any available media that can be accessed by computing device 600 and includes both volatile and nonvolatile media and removable and non-removable media. By way of example, and not limitation, computer readable media may comprise computer storage media and communication media. Computer storage media includes media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing device 600. Computer storage media, however, does not include communication media. Communication media embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of the any of the above should also be included within the scope of computer readable media.

Figure 6:
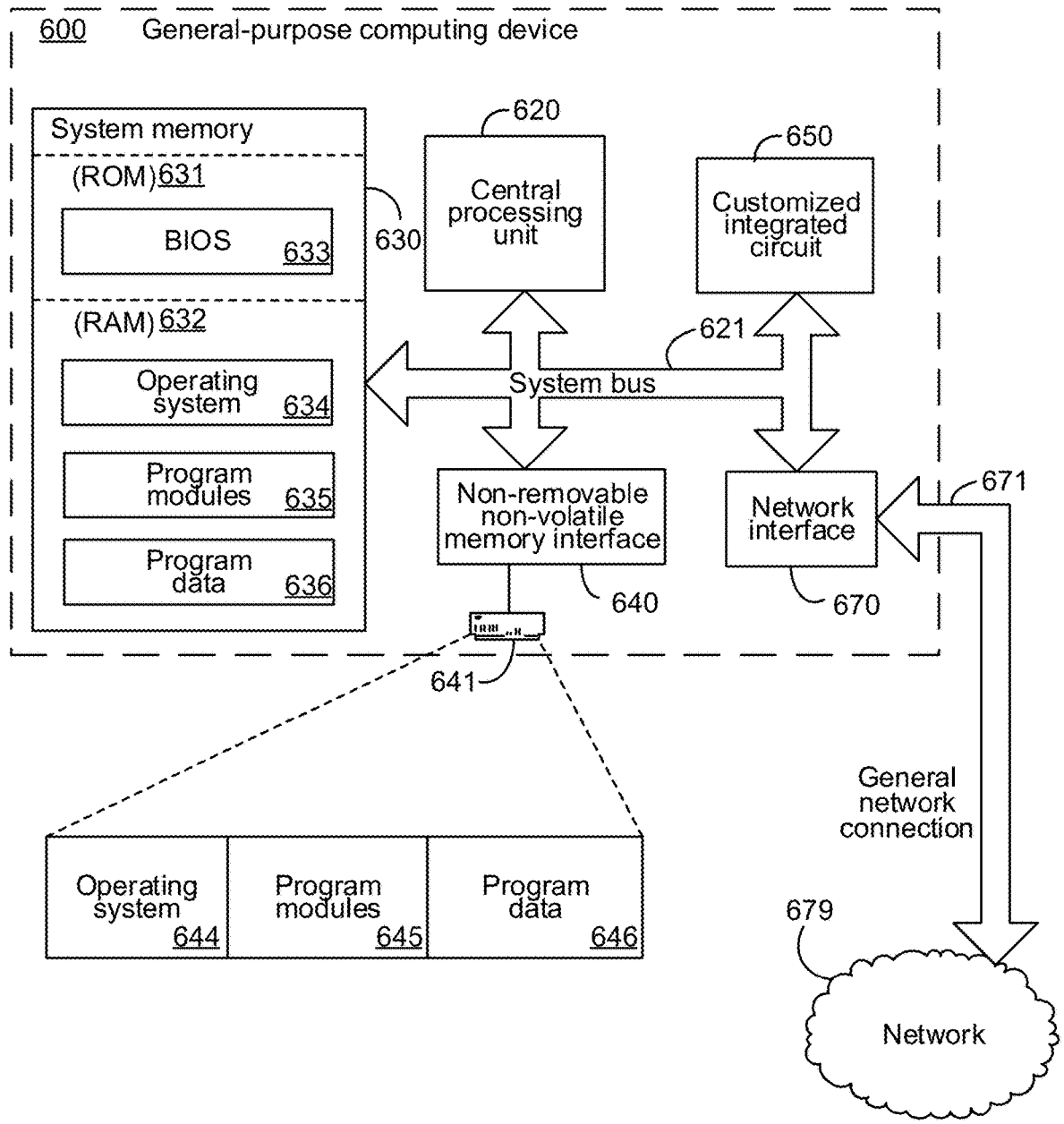
FIG. 6 is a block diagram of an exemplary computing device in which the exemplary customized circuit could be integrated.

The system memory 630 includes computer storage media in the form of volatile and/or nonvolatile memory such as read only memory (ROM) 631 and random access memory (RAM) 632. A basic input/output system 633 (BIOS), containing the basic routines that help to transfer information between elements within computing device 600, such as during start-up, is typically stored in ROM 631. RAM 632 typically contains data and/or program modules that are immediately accessible to and/or presently being operated on by processing unit 620. By way of example, and not limitation, FIG. 6 illustrates operating system 634, other program modules 635, and program data 636.

The computing device 600 may also include other removable/non-removable, volatile/nonvolatile computer storage media. By way of example only, FIG. 6 illustrates a hard disk drive 641 that reads from or writes to non-removable, nonvolatile magnetic media. Other removable/non-removable, volatile/nonvolatile computer storage media that can be used with the exemplary computing device include, but are not limited to, magnetic tape cassettes, flash memory cards, digital versatile disks, digital video tape, solid state RAM, solid state ROM, and other computer storage media, as defined and delineated above. The hard disk drive 641 is typically connected to the system bus 621 through a non-volatile memory interface such as interface 640.

The drives and their associated computer storage media discussed above and illustrated in FIG. 6, provide storage of computer readable instructions, data structures, program modules and other data for the computing device 600. In FIG. 6, for example, hard disk drive 641 is illustrated as storing operating system 644, other program modules 645, and program data 646. Note that these components can either be the same as or different from operating system 634, other program modules 635 and program data 636. Operating system 644, other program modules 645 and program data 646 are given different numbers hereto illustrate that, at a minimum, they are different copies.

The computing device 600 may operate in a networked environment using logical connections to one or more remote computers. The computing device 600 is illustrated as being connected to the general network connection 671 through a network interface or adapter 670, which is, in turn, connected to the system bus 621. In a networked environment, program modules depicted relative to the computing device 600, or portions or peripherals thereof, may be stored in the memory of one or more other computing devices that are communicatively coupled to the computing device 600 through the general network connection 671. It will be appreciated that the network connections shown are exemplary and other means of establishing a communications link between computing devices may be used.

Although described as a single physical device, the exemplary computing device 600 can be a virtual computing device, in which case the functionality of the above-described physical components, such as the CPU 620, the system memory 630, the network interface 670, and other like components can be provided by computer-executable instructions. Such computer-executable instructions can execute on a single physical computing device, or can be distributed across multiple physical computing devices, including being distributed across multiple physical computing devices in a dynamic manner such that the specific, physical computing devices hosting such computer-executable instructions can dynamically change over time depending upon need and availability. In the situation where the exemplary computing device 600 is a virtualized device, the underlying physical computing devices hosting such a virtualized computing device can, themselves, comprise physical components analogous to those described above, and operating in a like manner. Furthermore, virtual computing devices can be utilized in multiple layers with one virtual computing device executed within the construct of another virtual computing device. The term "computing device", therefore, as utilized herein, means either a physical computing device or a virtualized computing environment, including a virtual computing device, within which computer-executable instructions can be executed in a manner consistent with their execution by a physical computing device. Similarly, terms referring to physical components of the computing device, as utilized herein, mean either those physical components or virtualizations thereof performing the same or equivalent functions.

The descriptions above include, as a first example, a customized integrated circuit comprising: a calculation engine comprising circuitry that, during operation of the customized integrated circuit, enables the customized integrated circuit to generate a score of a single cell of a two-dimensional matrix based on generated scores of prior cells, a nucleotide, from one nucleotide sequence, that corresponds with the selected cell and a nucleotide from, another nucleotide sequence, that corresponds with the selected cell; and a first control unit comprising circuitry that, during operation of the customized integrated circuit, enables the customized integrated circuit to: select a cell of a first two-dimensional matrix, a first dimension of which is delineated by nucleotides of a first nucleotide sequence and a second dimension of which is delineated by nucleotides of a second nucleotide sequence, wherein a nucleotide from the first nucleotide sequence corresponds with the selected cell and a nucleotide from the second nucleotide sequence also corresponds with the selected cell; determine whether to instruct the calculation engine to generate a score of the selected cell based on a pre-determined threshold that demarcates between a first set of cells of the two-dimensional matrix for which scores are to be generated and a second set of cells of the two-dimensional matrix for which scores are not to be generated; instruct the calculation engine to generate the score of the selected cell, based on the selected cell being within the first set of cells, the instructing comprising providing, to the calculation engine, previously generated scores of prior cells, the nucleotide from the first nucleotide sequence that corresponds with the selected cell and the nucleotide from the second nucleotide sequence that corresponds with the selected cell; enter a zero score for the selected cell based on the selected cell being within the second set of cells; and repeat the selecting, the determining, the instructing and the entering for subsequent cells of the two-dimensional matrix.

A second example is the customized integrated circuit of the first example, wherein the pre-determined threshold extends diagonally through the two-dimensional matrix such that the second set of cells for which scores are not to be generated comprises a contiguous grouping of cells in a corner of the two-dimensional matrix.

A third example is the customized integrated circuit of the first example, wherein the pre-determined threshold is one of a first pre-determined threshold or a second pre-determined threshold, the first pre-determined threshold and the second pre-determined threshold extending diagonally through the two-dimensional matrix parallel to one another such that the first set of cells for which scores are to be generated comprises a contiguous grouping of cells extending diagonally from one corner of the two-dimensional matrix to an opposite corner of the two-dimensional matrix.

A fourth example is the customized integrated circuit of the first example, wherein the pre-determined threshold extends diagonally through a first portion of the two-dimensional matrix at a first angle and then extends diagonally through a second portion of the two-dimensional matrix at a second angle differing from the first angle.

A fifth example is the customized integrated circuit of the first example, further comprising a second control unit comprising circuitry that, during operation of the customized integrated circuit, enables the customized integrated circuit to: select a cell of a second, different two-dimensional matrix, a first dimension of which is delineated by nucleotides of a third nucleotide sequence and a second dimension of which is delineated by nucleotides of a fourth nucleotide sequence, wherein a nucleotide from the third nucleotide sequence corresponds with the selected cell and a nucleotide from the fourth nucleotide sequence also corresponds with the selected cell; determine whether to instruct the calculation engine to generate a score of the selected cell of the second two-dimensional matrix based on a second pre-determined threshold that demarcates between a first set of cells of the second two-dimensional matrix for which scores are to be generated and a second set of cells of the second two-dimensional matrix for which scores are not to be generated; instruct the calculation engine to generate the score of the selected cell of the second two-dimensional matrix, based on the selected cell of the second two-dimensional matrix being within the first set of cells of the second two-dimensional matrix, the instructing comprising providing, to the calculation engine, previously generated scores of prior cells of the second two-dimensional matrix, the nucleotide from the third nucleotide sequence that corresponds with the selected cell of the second two-dimensional matrix and the nucleotide from the fourth nucleotide sequence that corresponds with the selected cell of the second two-dimensional matrix; enter a zero score for the selected cell of the second two-dimensional matrix based on the selected cell being within the second set of cells of the second two-dimensional matrix; and repeat the selecting, the determining, the instructing and the entering for subsequent cells of the second two-dimensional matrix.

A sixth example is the customized integrated circuit of the fifth example, wherein the calculation engine generates scores for the first and second control units in an alternating manner including generating the score of the selected cell, as instructed by the first control unit, during a first processing cycle, and then generating the score of the selected cell of the second two-dimensional matrix, as instructed by the second control unit, during a second processing cycle immediately following the first processing cycle.

A seventh example is the customized integrated circuit of the first example, further comprising an input store unit, wherein the calculation engine obtains nucleotides of the first and second nucleotide sequences from the input store unit.

An eighth example is the customized integrated circuit of the seventh example, wherein the calculation engine generates the score of the single cell based on generated scores of prior cells as incremented by a gap-scoring factor, and wherein further the calculation engine obtains the gap-scoring factor from the input store unit.

A ninth example is the customized integrated circuit of the seventh example, wherein the first control unit obtains the pre-determined threshold from the input store unit.

A tenth example is the customized integrated circuit of the first example, further comprising a score aggregation unit comprising circuitry that, during operation of the customized integrated circuit, enables the customized integrated circuit to: receive the score of the single cell as generated by the calculation engine; and retain the score of the single cell if it is larger in value than a previously retained score of a prior cell.

An eleventh example is the customized integrated circuit of the first example, wherein the first control unit retains a quantity of immediately previously generated scores of immediately prior cells that is one greater than a quantity of nucleotides in one of the first or second nucleotide sequences, and wherein further the previously generated scores of prior cells that are provided, by the first control unit, to the calculation engine, are from the immediately previously generated scores of the immediately prior cells that are retained by the first control unit.

A twelfth example is the customized integrated circuit of the first example, further comprising a dispatching unit comprising circuitry that, during operation of the customized integrated circuit, enables the customized integrated circuit to: receive a first pair of nucleotide sequences to be compared to one another, the first pair of nucleotide sequences comprising the first and second nucleotide sequences; assign a first identifier to the first pair of nucleotide sequences; receive a second, different pair of nucleotides sequences to be compared to one another; assign a second identifier to the second pair of nucleotide sequences; provide the first pair of nucleotide sequences to a first comparison circuit comprising the calculation engine and the first control unit; provide the second pair of nucleotide sequences to a second comparison circuit; receive a first set of results from the first comparison circuit; receive a second set of results from the second comparison circuit after the receiving the first set of results; and reorder the second set of results ahead of the first set of results based on the assigned first and second identifiers.

A thirteenth example is the customized integrated circuit of the twelfth example, wherein the second comparison circuit comprises the calculation engine and a second control unit, and wherein further the calculation engine generates scores for the first and second control units in an alternating manner.

A fourteenth example is the customized integrated circuit of the first example, wherein the customized integrated circuit is an FPGA device.

A fifteenth example is a method of controlling a calculation engine that generates a score of a single cell of a two-dimensional matrix based on generated scores of prior cells, a nucleotide, from one nucleotide sequence, that corresponds with the selected cell and a nucleotide from, another nucleotide sequence, that corresponds with the selected cell, the method comprising the steps of: selecting a cell of a first two-dimensional matrix, a first dimension of which is delineated by nucleotides of a first nucleotide sequence and a second dimension of which is delineated by nucleotides of a second nucleotide sequence, wherein a nucleotide from the first nucleotide sequence corresponds with the selected cell and a nucleotide from the second nucleotide sequence also corresponds with the selected cell; determining whether to instruct the calculation engine to generate the score of the selected cell based on a pre-determined threshold that demarcates between a first set of cells of the two-dimensional matrix for which scores are to be generated and a second set of cells of the two-dimensional matrix for which scores are not to be generated; instructing the calculation engine to generate a score of the selected cell, based on the selected cell being within the first set of cells, the instructing comprising providing, to the calculation engine, previously generated scores of prior cells, the nucleotide from the first nucleotide sequence that corresponds with the selected cell and the nucleotide from the second nucleotide sequence that corresponds with the selected cell; entering a zero score for the selected cell based on the selected cell being within the second set of cells; and repeating the selecting, the determining, the instructing and the entering for subsequent cells of the two-dimensional matrix.

A sixteenth example is the method of the fifteenth example, wherein the pre-determined threshold extends diagonally through the two-dimensional matrix such that the second set of cells for which scores are not to be generated comprises a contiguous grouping of cells in a corner of the two-dimensional matrix.

A seventeenth example is the method of the fifteenth example, wherein the pre-determined threshold extends diagonally through a first portion of the two-dimensional matrix at a first angle and then extends diagonally through a second portion of the two-dimensional matrix at a second angle differing from the first angle.

An eighteenth example is the method of the fifteenth example, further comprising: selecting a cell of a second, different two-dimensional matrix, a first dimension of which is delineated by nucleotides of a third nucleotide sequence and a second dimension of which is delineated by nucleotides of a fourth nucleotide sequence, wherein a nucleotide from the third nucleotide sequence corresponds with the selected cell and a nucleotide from the fourth nucleotide sequence also corresponds with the selected cell; determining whether to instruct the calculation engine to generate a score of the selected cell of the second two-dimensional matrix based on a second pre-determined threshold that demarcates between a first set of cells of the second two-dimensional matrix for which scores are to be generated and a second set of cells of the second two-dimensional matrix for which scores are not to be generated; instructing the calculation engine to generate a score of the selected cell of the second two-dimensional matrix, based on the selected cell of the second two-dimensional matrix being within the first set of cells of the second two-dimensional matrix, the instructing comprising providing, to the calculation engine, previously generated scores of prior cells of the second two-dimensional matrix, the nucleotide from the third nucleotide sequence that corresponds with the selected cell of the second two-dimensional matrix and the nucleotide from the fourth nucleotide sequence that corresponds with the selected cell of the second two-dimensional matrix; entering a zero score for the selected cell of the second two-dimensional matrix based on the selected cell being within the second set of cells of the second two-dimensional matrix; and repeating the selecting, the determining, the instructing and the entering for subsequent cells of the second two-dimensional matrix; wherein the instructing the calculation engine to generate a score of the selected cell and the instructing the calculation engine to generate a score of the selected cell of the second two-dimensional matrix are performed in an alternating manner.

A nineteenth example is the method of the fifteenth example: further comprising: retaining a quantity of immediately previously generated scores of immediately prior cells that is one greater than a quantity of nucleotides in one of the first or second nucleotide sequences.

A twentieth example is a computing device comprising one or more processing units; and one or more computer-readable storage media comprising computer-executable instructions, which, when executed by the one or more processing units, cause the computing device to: select a cell of a first two-dimensional matrix, a first dimension of which is delineated by nucleotides of a first nucleotide sequence and a second dimension of which is delineated by nucleotides of a second nucleotide sequence, wherein a nucleotide from the first nucleotide sequence corresponds with the selected cell and a nucleotide from the second nucleotide sequence also corresponds with the selected cell; determine whether to generate a score of the selected cell based on a pre-determined threshold that demarcates between a first set of cells of the two-dimensional matrix for which scores are to be generated and a second set of cells of the two-dimensional matrix for which scores are not to be generated; generate, based on the selected cell being within the first set of cells, the score of the selected cell, the score being a function of previously generated scores of prior cells, the nucleotide from the first nucleotide sequence that corresponds with the selected cell and the nucleotide from the second nucleotide sequence that corresponds with the selected cell; enter a zero score for the selected cell based on the selected cell being within the second set of cells; and repeat the selecting, the determining, the generating and the entering for subsequent cells of the two-dimensional matrix.

As can be seen from the above descriptions, customized integrated circuits for comparing two nucleotide sequences in series have been presented. In view of the many possible variations of the subject matter described herein, we claim as our invention all such embodiments as may come within the scope of the following claims and equivalents thereto.

We claim:

1. A customized integrated circuit comprising:
a calculation engine comprising circuitry that, during operation of the customized integrated circuit, enables the customized integrated circuit to
generate a score of a single cell of a two-dimensional matrix based on: generated scores of vertically prior cells in a column, of the two-dimensional matrix, comprising the single cell, generated scores of horizontally prior cells in a row, of the two-dimensional matrix, comprising the single cell, a nucleotide, from one nucleotide sequence, that corresponds with the selected cell, and a nucleotide from, another nucleotide sequence, that corresponds with the selected cell; and
a first control unit comprising circuitry that, during operation of the customized integrated circuit, enables the customized integrated circuit to:
select a cell of a first two-dimensional matrix, a first dimension of which is delineated by nucleotides of a first nucleotide sequence and a second dimension of which is delineated by nucleotides of a second nucleotide sequence, wherein a nucleotide from the first nucleotide sequence corresponds with the selected cell and a nucleotide from the second nucleotide sequence also corresponds with the selected cell;
determine whether to instruct the calculation engine to generate a score of the selected cell based on a pre-determined threshold that demarcates between a first set of cells of the two-dimensional matrix for which scores are to be generated and a second set of cells of the two-dimensional matrix for which scores are not to be generated;
instruct the calculation engine to generate the score of the selected cell, based on the selected cell being within the first set of cells, the instructing comprising providing, to the calculation engine, previously generated scores of prior cells, the nucleotide from the first nucleotide sequence that corresponds with the selected cell and the nucleotide from the second nucleotide sequence that corresponds with the selected cell;
enter a zero score for the selected cell based on the selected cell being within the second set of cells; and
repeat the selecting, the determining, the instructing and the entering for subsequent cells, in series, of the two-dimensional matrix.

2. The customized integrated circuit of claim 1, wherein the pre-determined threshold extends diagonally through the two-dimensional matrix such that the second set of cells for which scores are not to be generated comprises a contiguous grouping of cells in a corner of the two-dimensional matrix.

3. The customized integrated circuit of claim 1, wherein the pre-determined threshold is one of a first pre-determined threshold or a second pre-determined threshold, the first pre-determined threshold and the second pre-determined threshold extending diagonally through the two-dimensional matrix parallel to one another such that the first set of cells for which scores are to be generated comprises a contiguous grouping of cells extending diagonally from one corner of the two-dimensional matrix to an opposite corner of the two-dimensional matrix.

4. The customized integrated circuit of claim 1, wherein the pre-determined threshold extends diagonally through a first portion of the two-dimensional matrix at a first angle and then extends diagonally through a second portion of the two-dimensional matrix at a second angle differing from the first angle.

5. The customized integrated circuit of claim 1, further comprising a second control unit comprising circuitry that, during operation of the customized integrated circuit, enables the customized integrated circuit to:
select a cell of a second, different two-dimensional matrix, a first dimension of which is delineated by nucleotides of a third nucleotide sequence and a second dimension of which is delineated by nucleotides of a fourth nucleotide sequence, wherein a nucleotide from the third nucleotide sequence corresponds with the selected cell and a nucleotide from the fourth nucleotide sequence also corresponds with the selected cell;
determine whether to instruct the calculation engine to generate a score of the selected cell of the second two-dimensional matrix based on a second pre-determined threshold that demarcates between a first set of cells of the second two-dimensional matrix for which scores are to be generated and a second set of cells of the second two-dimensional matrix for which scores are not to be generated;

instruct the calculation engine to generate the score of the selected cell of the second two-dimensional matrix, based on the selected cell of the second two-dimensional matrix being within the first set of cells of the second two-dimensional matrix, the instructing comprising providing, to the calculation engine, previously generated scores of prior cells of the second two-dimensional matrix, the nucleotide from the third nucleotide sequence that corresponds with the selected cell of the second two-dimensional matrix and the nucleotide from the fourth nucleotide sequence that corresponds with the selected cell of the second two-dimensional matrix;

enter a zero score for the selected cell of the second two-dimensional matrix based on the selected cell being within the second set of cells of the second two-dimensional matrix; and repeat the selecting, the determining, the instructing and the entering for subsequent cells of the second two-dimensional matrix.

6. The customized integrated circuit of claim 5, wherein the calculation engine generates scores for the first and second control units in an alternating manner including generating the score of the selected cell, as instructed by the first control unit, during a first processing cycle, and then generating the score of the selected cell of the second two-dimensional matrix, as instructed by the second control unit, during a second processing cycle immediately following the first processing cycle.

7. The customized integrated circuit of claim 1, further comprising an input store unit, wherein the calculation engine obtains nucleotides of the first and second nucleotide sequences from the input store unit.

8. The customized integrated circuit of claim 7, wherein the calculation engine generates the score of the single cell based on generated scores of prior cells as incremented by a gap-scoring factor, and wherein further the calculation engine obtains the gap-scoring factor from the input store unit.

9. The customized integrated circuit of claim 7, wherein the first control unit obtains the pre-determined threshold from the input store unit.

10. The customized integrated circuit of claim 1, further comprising a score aggregation unit comprising circuitry that, during operation of the customized integrated circuit, enables the customized integrated circuit to:

receive the score of the single cell as generated by the calculation engine; and retain the score of the single cell if it is larger in value than a previously retained score of a prior cell.

11. The customized integrated circuit of claim 1, wherein the first control unit retains a quantity of immediately previously generated scores of immediately prior cells that is one greater than a quantity of nucleotides in one of the first or second nucleotide sequences, and wherein further the previously generated scores of prior cells that are provided, by the first control unit, to the calculation engine, are from the immediately previously generated scores of the immediately prior cells that are retained by the first control unit.

12. The customized integrated circuit of claim 1, further comprising a dispatching unit comprising circuitry that, during operation of the customized integrated circuit, enables the customized integrated circuit to:

receive a first pair of nucleotide sequences to be compared to one another, the first pair of nucleotide sequences comprising the first and second nucleotide sequences;

assign a first identifier to the first pair of nucleotide sequences;

receive a second, different pair of nucleotides sequences to be compared to one another;

assign a second identifier to the second pair of nucleotide sequences;

provide the first pair of nucleotide sequences to a first comparison circuit comprising the calculation engine and the first control unit;

provide the second pair of nucleotide sequences to a second comparison circuit;

receive a first set of results from the first comparison circuit;

receive a second set of results from the second comparison circuit after the receiving the first set of results; and reorder the second set of results ahead of the first set of results based on the assigned first and second identifiers.

13. The customized integrated circuit of claim 12, wherein the second comparison circuit comprises the calculation engine and a second control unit, and wherein further the calculation engine generates scores for the first and second control units in an alternating manner.

14. The customized integrated circuit of claim 1, wherein the customized integrated circuit is an FPGA device.

15. A method of controlling a calculation engine that generates a score of a single cell of a two-dimensional matrix based on generated scores of vertically prior cells in a column, of the two-dimensional matrix, comprising the single cell, generated scores of horizontally prior cells in a row, of the two-dimensional matrix, comprising the single cell, a nucleotide, from one nucleotide sequence, that corresponds with the selected cell, and a nucleotide from, another nucleotide sequence, that corresponds with the selected cell, the method comprising the steps of:

selecting a cell of a first two-dimensional matrix, a first dimension of which is delineated by nucleotides of a first nucleotide sequence and a second dimension of which is delineated by nucleotides of a second nucleotide sequence, wherein a nucleotide from the first nucleotide sequence corresponds with the selected cell and a nucleotide from the second nucleotide sequence also corresponds with the selected cell;

determining whether to instruct the calculation engine to generate the score of the selected cell based on a pre-determined threshold that demarcates between a first set of cells of the two-dimensional matrix for which scores are to be generated and a second set of cells of the two-dimensional matrix for which scores are not to be generated;

instructing the calculation engine to generate a score of the selected cell, based on the selected cell being within the first set of cells, the instructing comprising providing, to the calculation engine, previously generated scores of prior cells, the nucleotide from the first nucleotide sequence that corresponds with the selected cell and the nucleotide from the second nucleotide sequence that corresponds with the selected cell;

entering a zero score for the selected cell based on the selected cell being within the second set of cells; and repeating the selecting, the determining, the instructing and the entering for subsequent cells, in series, of the two-dimensional matrix.

16. The method of claim 15, wherein the pre-determined threshold extends diagonally through the two-dimensional matrix such that the second set of cells for which scores are not to be generated comprises a contiguous grouping of cells in a corner of the two-dimensional matrix.

17. The method of claim 15, wherein the pre-determined threshold extends diagonally through a first portion of the two-dimensional matrix at a first angle and then extends diagonally through a second portion of the two-dimensional matrix at a second angle differing from the first angle.

18. The method of claim 15, further comprising:
selecting a cell of a second, different two-dimensional matrix, a first dimension of which is delineated by nucleotides of a third nucleotide sequence and a second dimension of which is delineated by nucleotides of a fourth nucleotide sequence, wherein a nucleotide from the third nucleotide sequence corresponds with the selected cell and a nucleotide from the fourth nucleotide sequence also corresponds with the selected cell;
determining whether to instruct the calculation engine to generate a score of the selected cell of the second two-dimensional matrix based on a second pre-determined threshold that demarcates between a first set of cells of the second two-dimensional matrix for which scores are to be generated and a second set of cells of the second two-dimensional matrix for which scores are not to be generated;
instructing the calculation engine to generate a score of the selected cell of the second two-dimensional matrix, based on the selected cell of the second two-dimensional matrix being within the first set of cells of the second two-dimensional matrix, the instructing comprising providing, to the calculation engine, previously generated scores of prior cells of the second two-dimensional matrix, the nucleotide from the third nucleotide sequence that corresponds with the selected cell of the second two-dimensional matrix and the nucleotide from the fourth nucleotide sequence that corresponds with the selected cell of the second two-dimensional matrix;
entering a zero score for the selected cell of the second two-dimensional matrix based on the selected cell being within the second set of cells of the second two-dimensional matrix; and
repeating the selecting, the determining, the instructing and the entering for subsequent cells of the second two-dimensional matrix;

wherein the instructing the calculation engine to generate a score of the selected cell and the instructing the calculation engine to generate a score of the selected cell of the second two-dimensional matrix are performed in an alternating manner.

19. The method of claim 15, further comprising:
retaining a quantity of immediately previously generated scores of immediately prior cells that is one greater than a quantity of nucleotides in one of the first or second nucleotide sequences.

20. A computing device comprising
one or more processing units comprising circuitry; and
one or more computer-readable storage media comprising computer-executable instructions, which, when executed by the one or more processing units, cause the computing device to:
select a cell of a two-dimensional matrix, a first dimension of which is delineated by nucleotides of a first nucleotide sequence and a second dimension of which is delineated by nucleotides of a second nucleotide sequence, wherein a nucleotide from the first nucleotide sequence corresponds with the selected cell and a nucleotide from the second nucleotide sequence also corresponds with the selected cell;
determine whether to generate a score of the selected cell based on a pre-determined threshold that demarcates between a first set of cells of the two-dimensional matrix for which scores are to be generated and a second set of cells of the two-dimensional matrix for which scores are not to be generated;
generate, based on the selected cell being within the first set of cells, the score of the selected cell, the score being a function of: previously generated scores of vertically prior cells in a column, of the two-dimensional matrix, comprising the single cell, previously generated scores of horizontally prior cells in a row, of the two-dimensional matrix, comprising the single cell, the nucleotide from the first nucleotide sequence that corresponds with the selected cell, and the nucleotide from the second nucleotide sequence that corresponds with the selected cell;
enter a zero score for the selected cell based on the selected cell being within the second set of cells; and
repeat the selecting, the determining, the generating and the entering for subsequent cells, in series, of the two-dimensional matrix.

* * * * *